(12) United States Patent
Sabesan

(10) Patent No.: US 7,381,715 B2
(45) Date of Patent: Jun. 3, 2008

(54) ANTIMICROBIAL SOLID SURFACE MATERIALS CONTAINING CHITOSAN-METAL COMPLEXES

(75) Inventor: Subramaniam Sabesan, Wilmington, DE (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 366 days.

(21) Appl. No.: 10/999,672

(22) Filed: Nov. 30, 2004

(65) Prior Publication Data

US 2005/0154361 A1   Jul. 14, 2005

Related U.S. Application Data

(63) Continuation-in-part of application No. 10/324,803, filed on Dec. 20, 2002, now abandoned.

(60) Provisional application No. 60/343,321, filed on Dec. 21, 2001.

(51) Int. Cl.
*A61K 31/722* (2006.01)
*A61K 33/38* (2006.01)
*A01N 59/16* (2006.01)
*D06M 15/03* (2006.01)
*C08L 5/08* (2006.01)
*C08B 37/08* (2006.01)

(52) U.S. Cl. .............. 514/55; 514/964; 424/404; 424/447; 424/484; 8/115.51; 106/162.2

(58) Field of Classification Search ............... 514/55
See application file for complete search history.

(56) References Cited

U.S. PATENT DOCUMENTS

| | | | |
|---|---|---|---|
| 3,389,549 A | 6/1968 | David | |
| 3,567,632 A | 3/1971 | Richter et al. | |
| 3,847,865 A | 11/1974 | Duggins | |
| 4,085,246 A | 4/1978 | Buser et al. | |
| 4,595,708 A | 6/1986 | Sundet | |
| 5,541,233 A | 7/1996 | Roenigk | |
| 5,559,205 A | 9/1996 | Hansen et al. | |
| 5,607,765 A | 3/1997 | Hansen et al. | |
| 5,643,971 A | 7/1997 | Roenigk | |
| 6,663,877 B1 | 12/2003 | Appleton et al. | |
| 2003/0017194 A1 | 1/2003 | Jociger et al. | |
| 2003/0091612 A1 | 5/2003 | Sabesan et al. | |
| 2004/0243041 A1* | 12/2004 | Qin et al. .......... | 602/41 |
| 2005/0118239 A1 | 6/2005 | Sabesan | |

FOREIGN PATENT DOCUMENTS

| | | |
|---|---|---|
| EP | 1139470 | 10/2001 |
| JP | 7-266522 | 10/1995 |
| JP | 8-113674 | 5/1996 |
| JP | 08-268821 | * 10/1996 |
| WO | WO97/49761 | 12/1997 |
| WO | WO99/37584 | 7/1999 |
| WO | 01/80912 | * 11/2001 |

OTHER PUBLICATIONS

HCAPLUS Abstract 1999:18659 (1999).*
S.N. Chirkov, The Antiviral Activity of Chitosan (Review), Applied Biochemistry and Microbiology, vol. 38, No. 1 (2002), pp. 1-8.
Tyrone L. Vigo, Antimicrobial Polymers and Fibers: Retrospective and Prospective, Bioactive Fibers and Polymers, ACS Symposium Series 792, pp. 175-201, Amer Chem Soc (2001).
C. Peniche-Covas and M.S. Jimenez, Characterization of Silver-Binding Chitosan by Thermal Analysis and Electron Impact Mass Spectrometry, Carb Polymers, 9 (1988) pp. 249-256.
L. Mackenzie Miall and D.W.A. Sharp, A New Dictionary of Chemistry, 4th edition, p. 157 (1968).
Mark HF and Knoschwitz, eds. Encyclopedia of Polymer Science and Technology, 2nd ed., vol. 8, pp. 393-396.
Bowmans PWJM, Industively Coupled Plasma Emission Spectroscopy. John Wiley & Sons (New York, NY), 1987, pp. 2-3.
Carol L. Lasko et al., An Investigation Into the Use of Chitosan for the Removal of Soluble Silver From Industrial Wastewater, Environ. Sci. Technol., vol. 33:3622-3626, 1999.
Z. G. Hu et al., New Preparation of Chitosan/Silver Nanocomposite and its Antibacterial Activity on Cotton, Polymer Preprints, vol. 46(2):767-768, 2005.
Haizhen Huang et al., Preparation and Characterization of Metal-Chitosan Nanocomposites, Colloids and Surfaces B:Biointerfaces, vol. 39:31-37, 2004.
Daming Cheng et al., Facile Fabrication of AGCL@Polypyrrole-Chitosan Core-Shell Nanoparticles and Polymeric Hollow Nanospheres, Langmuir, vol. 20:9909-9912, 2004.

* cited by examiner

*Primary Examiner*—John Pak

(57) ABSTRACT

A solid surface material with an antimicrobial agent in a thermoset and/or thermoplastic resin matrix where the antimicrobial agent comprises a chitosan-metal complex.

4 Claims, 15 Drawing Sheets

ANTIMICROBIAL SOLID SURFACE MATERIALS CONTAINING CHITOSAN-METAL COMPLEXES

CROSS-REFERENCE TO RELATED APPLICATIONS

This is a continuation-in-part of U.S. patent application Ser. No. 10/324,803 filed Dec. 20, 2002 now abandoned, which claims the benefit of Provisional Application No. 60/343,321 filed Dec. 21, 2001, both of which are hereby incorporated by reference.

FIELD OF INVENTION

This invention is directed to solid surface materials having antimicrobial properties.

BACKGROUND OF THE INVENTION

Artificial or synthetic marble is a general designation for various types of materials used as building products, such as bathroom vanity tops, sinks, shower stalls and kitchen counter tops, and other decorative surfaces. It is also a suitable material for use in furniture, lining materials, and in stationary small articles. The artificial marble is easily kept clean and neat. Therefore, it has increasingly been used in hospitals, nursing homes, as well as in commercial and residential food preparation facilities.

Artificial marbles encompass cultured marble, onyx and solid surface materials typically comprising some kind of resin matrix and either with or without a filler present in the resin matrix. Typically, cultured marble is made of a gel coating of unfilled unsaturated polyester on a substrate of a filled unsaturated polyester. The filler may be calcium carbonate or a similar material. Onyx typically consists of a gel coat of unfilled unsaturated polyester on a substrate of filled unsaturated polyester. The filler in this case is typically alumina trihydrate (ATH). Solid surface materials are typically filled resin materials and, unlike cultured marble or onyx, do not have a gel coat. Corian® material available from E. I. du Pont de Nemours and Company (DuPont), Wilmington, Del., is a solid surface material comprising an acrylic matrix filled with ATH. Another solid surface DuPont material, known by the brand name Zodiaq®, is alternatively described as an engineered stone or artificial granite. Such materials are made from an unsaturated polyester matrix filled with quartz or other similar fillers.

As evidenced by numerous materials in the market, there is clearly a demand for materials and/or processes that either minimize or kill harmful microorganisms encountered in the environment. Such materials are useful in areas for food preparation, processing, service or handling. Such materials will also be useful in areas for personal hygiene, such as bathroom facilities. Similarly, there is a use for such antimicrobial materials in hospitals and nursing homes where people with lowered resistance are especially vulnerable to pathogenic microorganisms.

Solid surface materials made of either an acrylic resin, an unsaturated polyester resin, an epoxy resin, or other such resins and incorporating certain antimicrobial agents throughout the resin are described in WO 97/49761 (E. I. du Pont de Nemours and Company). However, such antimicrobial agents can be expensive, resulting in a high installation cost for the resulting solid surface material.

Chitosan and chitosan-metal compounds are known to provide antimicrobial activity as bacteriocides and fungicides (see, e.g., T. L. Vigo, "Antimicrobial Polymers and Fibers: Retrospective and Prospective," in *Bioactive Fibers and Polymers*, J. V. Edwards and T. L. Vigo, eds., ACS Symposium Series 792, pp. 175-200, American Chemical Society, 2001). Chitosan is also known to impart antiviral activity, though the mechanism is not yet well understood (see, e.g., Chirkov, S. N., Applied Biochemistry and Microbiology (Translation of Prikladnaya Biokhimiya i Mikrobiologiya) (2002), 38(1), 1-8).

Chitosan is the commonly used name for poly-[1-4]-β-D-glucosamine. Chitosan is chemically derived from chitin (a poly-[1-4]-β-N-acetyl-D-glucosamine) which, in turn, is derived from the cell walls of fungi, the shells of insects, and, especially, crustaceans. Thus, it is inexpensively derived from widely available materials. It is available as an article of commerce from, for example, Primex (Iceland); Biopolymer Engineering, Inc. (St. Paul, Minn.); Biopolymer Technologies, Inc. (Westborough, Mass.); and CarboMer, Inc. (Westborough, Mass.). Chitosan can also be treated with metal-salt solutions so that the metal ion forms a complex with the chitosan. For example, U.S. Pat. Nos. 5,541,233 and 5,643,971 disclose a process for preparing durable antimicrobial agents by treating a chitosan suspension with metal salts of zinc and copper followed by chelation of a potentiator such as an imidazole. Application WO 99/37584 discloses the preparation of chitosan-zinc sulfate, copper sulfate and silver nitrate complexes for treating water to reduce levels of pathogens.

In commonly assigned U.S. patent application Ser. No. 60/290,297 (filed 11 May 2001), chitosan (in the form of an acidic solution applied to polyester articles) is shown to impart antimicrobial activity. The chitosan-treated article may be treated subsequently with a solution of zinc sulfate, cupric sulfate, or silver nitrate to enhance antimicrobial activity.

Cultured marbles have been developed incorporating an antimicrobial agent in the gel coat only (i.e., not throughout the matrix of the substrate). Such materials have been disclosed in Japanese Patent Application Publication Kokai: 7-266522. These materials have a relatively thin gel coat, typically on the order of 15 mils. As such, when the gel coat is depleted of antimicrobial agent or the gel coat wears away or is otherwise removed, the antimicrobial effect of the gel coat is significantly decreased or lost entirely.

The problem that remains to be solved is to provide solid surface materials comprising either an acrylic resin, an unsaturated polyester resin, an epoxy or other similar resin and an effective antimicrobial agent dispersed throughout the resin.

SUMMARY OF THE INVENTION

This invention is directed to a solid surface material comprising a matrix of at least one resin, and an antimicrobial agent dispersed in the matrix. The antimicrobial agent is a chitosan-metal complex, which is prepared under homogeneous conditions and isolated as a product. The resin can be thermoset, thermoplastic, or combinations thereof. Optionally, at least one filler can be dispersed in the matrix.

In a preferred embodiment, the resin is made from a syrup comprising an acrylic group polymer dissolved in a material selected from the group of an acrylic group monomer solution and a mixed monomer solution containing a vinyl monomer for copolymerization with an acrylic group monomer as a main component; the filler is alumina trihydrate; and the antimicrobial agent comprises a complex of chitosan with silver or a silver compound.

DETAILED DESCRIPTION OF THE PREFERRED EMBODIMENTS

Figure 1:
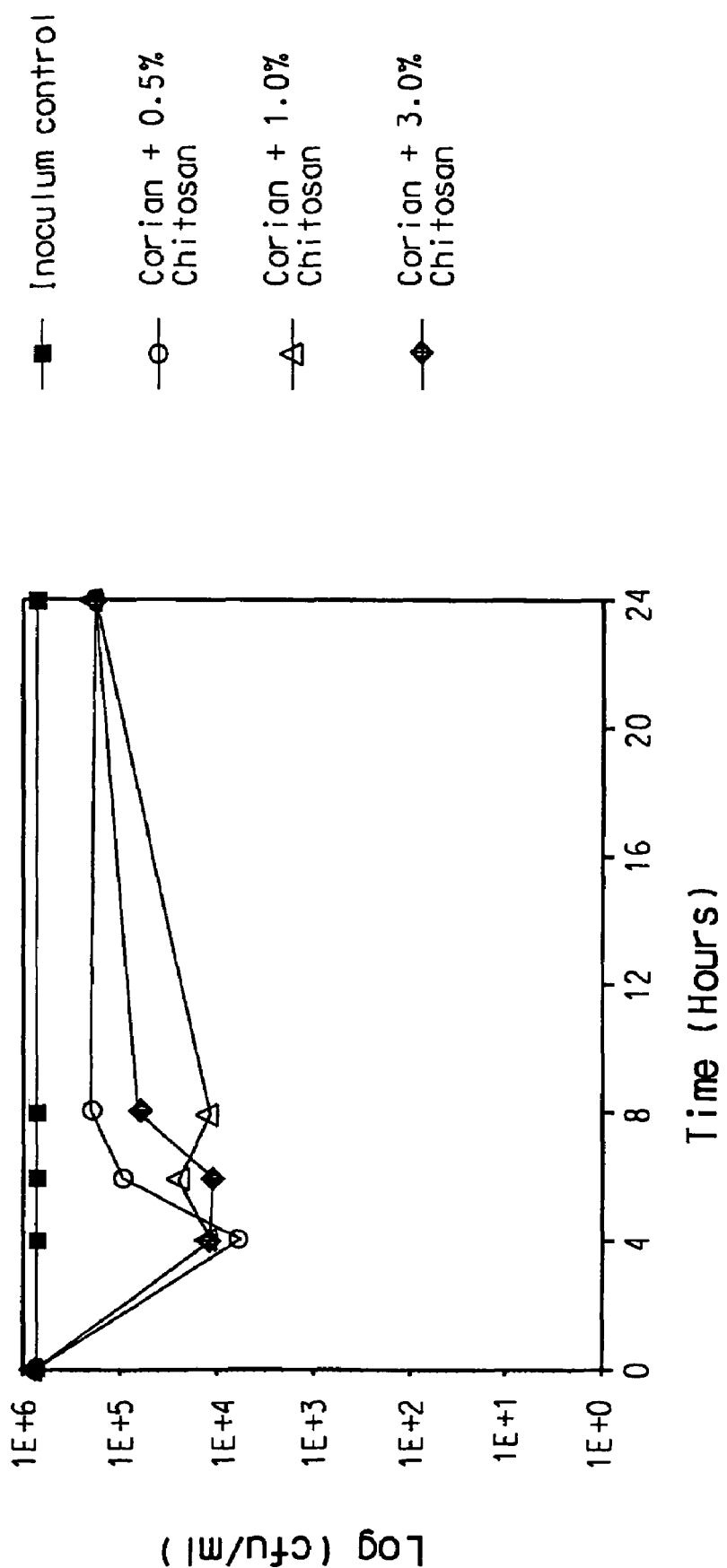
FIG. 1 shows the results of Corian® material with 0.5%, 1.0%, and 3.0% chitosan content vs. *Escherichia coli* (ATCC 25922).

The artificial marbles of the present invention are made from a curable resin composition containing a chitosan-metal complex as an antimicrobial agent. As used herein, by the term "complex" is meant a compound in which the bonding occurs by interaction of the electrons of the donor with the empty orbitals of the acceptor. In some complexes, the electron flow may take place in both directions simultaneously. (*A New Dictionary of Chemistry*, Fourth Edition, L. M. Miall and D. W. A. Sharo (eds.), John Wiley & Sons, Inc., New York, N.Y. (1968), p. 157). The preferred embodiment of the invention comprises a chitosan-silver complex.

The artificial marble materials of this invention are effective in inhibiting or destroying many common harmful microorganisms encountered in the home, health care, and food preparation environments. Microorganisms commonly found in such environments, particularly when such environments remain wet, moist, or damp, include bacteria, yeasts, fungi, and viruses. Examples include, but are not limited to, *Escherichia coli, Candida albicans, Staphylococcus aureus, Salmonella cholerasuis, Listeria weshimeri*, and *Klebsiella pneumoniae*.

The present invention is directed to antimicrobial solid surfaces. By "antimicrobial" herein is meant bacteriocidal, fungicidal, and antiviral. The term "microbe" will similarly be used to mean a bacterium, fungus, or virus. The term "antimicrobial effectiveness" is intended to mean that, given a sufficient amount of antimicrobial agent, the microbial concentration of a sample is decreased by at least a 3-log factor (i.e., 99.9%) over a period of time. The actual antimicrobial effectiveness of an antimicrobial agent depends upon the specific resin matrix used and the specific bacteria tested.

The term "solid surface materials" herein refers to materials that are essentially non-porous composites of finely divided mineral fillers dispersed in an organic polymer matrix. As used herein, the term "organic polymer matrix" is synonymous with "resin matrix". Solid surface materials include, for example, materials useful for decorative solid surfaces such as, for example, those used as building products such as bathroom vanity tops, sinks, shower stalls and kitchen countertops. Furniture, sanitary use, lining materials, and various articles such as office supplies and store fixtures may also be constructed of solid surface materials.

Resin Matrix Materials

Solid surface materials comprise a resin matrix. The term "matrix" as used herein refers to the polymeric resin component in which fillers and other additives may be dispersed. The types of resin matrices useful in the present invention include thermoplastic resins, thermoset resins, and combinations thereof. Thermoplastic resins include olefins (such as low and high-density polyethylene and polypropylene), dienes (such as polybutadiene and Neoprene® elastomer), vinyl polymers (such as polystyrene, acrylics, and polyvinyl chloride), fluoropolymers (such as polytetrafluoroethylene), and heterochain polymers (such as polyamides, polyesters, polyurethanes, polyethers, polyacetals and polycarbonates). Thermoset resins include phenolic resins, amino resins, unsaturated polyester resins, epoxy resins, polyurethanes, and silicone polymers.

Epoxy resins useful in the present invention include epoxy resins of bisphenol type A, bisphenol type F, phenol novolak type, alicyclic epoxy, halogenated epoxy, and cycloaliphatic epoxy resins.

Unsaturated polyester resins useful in the present invention include those wherein the reactivity is based on the presence of double or triple bonds in the carbon atoms. Unsaturated polyester resins are formed by the reaction of molar amounts of unsaturated and saturated dibasic acids or anhydrides with glycols. The unsaturation sites can then be used to cross-link the polyester chains, via vinyl-containing monomers such as but not limited to styrene, MMA, or combinations of styrene/MMA into a thermoset plastic state.

As is known to those of ordinary skill in the art, there can be many additives to epoxy or unsaturated polyesters. Typically, such materials are cured by adding cross-linking agents and catalysts to enhance the cross-linking action.

Acrylic resins useful in the present invention are not limited as long as the resin can be formed into an acrylic solid surface material by curing. Examples of useful acrylic resins include various kinds of conventional acrylic group monomers, acrylic group partial polymers, vinyl monomers for copolymerization other than acrylic group monomers, or partial polymers. As the acrylic group monomer, (meth) acrylic ester is preferable. As used herein, "(meth)acrylic" is understood to mean "acrylic and/or methacrylic". Examples of (meth)acrylic esters include methyl (meth)acrylic ester, ethyl (meth)acrylic ester, butyl (meth)acrylic ester, 2-ethyl-hexyl (meth)acrylic ester, benzyl (meth)acrylic ester, glycidyl (meth)acrylic ester.

An example of a useful solid surface material including acrylic resin is the Corian® material, which includes a poly(methyl methacrylate) (PMMA) resin with ATH as a filler. Another example of a useful solid surface material is Zodiaq® material, which comprises an unsaturated polyester (UPE) resin with a quartz or other silica filler. Both Corian® material and Zodiaq® material can contain pigments, reground self material in particulate form, and other additives as disclosed in U.S. Pat. Nos. 3,847,865 and 4,085,246, both incorporated by reference herein.

Antimicrobial Agent

The solid surface materials of the present invention comprise at least one antimicrobial agent that is dispersed in the resin matrix of the solid surface material in an amount that provides the solid surface material with an antimicrobial effectiveness as measured at an outer surface. The term "dispersed" herein means that the antimicrobial agent of the invention is present throughout the bulk of the solid surface material of the invention and not just on the surface of the solid surface material. The antimicrobial agent is provided in an amount that results in antimicrobial effectiveness, i.e., a 3-log reduction in the number of microorganisms, within about 24 hours from application as measured by the "Antimicrobial Hard Surface Test" and "Antimicrobial Hard Surface Wipe Test" methods described below.

The amount of antimicrobial agent is preferably at least about 0.5 to 8% by weight of the precured total composition and, more preferably, at least about 1% by weight of the precured total composition. It is preferred that the antimicrobial agent be added and dispersed into the resin component. Chitosan-silver complex, for example, may be added to the MMA before polymerization. Chitosan-silver complex may be added to the UPE before mixing with quartz or other silica and then vibrocompacted. Further processing (polymerization) does not alter the antimicrobial features of the agent.

The antimicrobial agent comprises a complex of chitosan and a metal, preferably silver, copper, or zinc. The metal or metal compounds can be present in amounts of 1% to 14% by weight based on the chitosan. These materials were ground to about 400 mesh size for use as additives in the preparation of polymers. While 400 mesh size was used for the embodiments of the Examples, the range of the particle size may be from about 100 mesh and smaller. Chitosan-silver complex is preferred for its superior antimicrobial efficacy.

The chitosan-silver complex used in the present invention is prepared by slowly adding a solution of silver salt to a chitosan solution such that a clear, colorless gel results. Typically, the silver salt solution is 0.5 to 20 wt % silver nitrate in water. The chitosan solution comprises 0.25% to 8.0% by weight chitosan in a dilute (0.25 to 5.0% by volume) aqueous solution of acetic acid. Typically, the chitosan is a 0.75% or 1.5% by volume aqueous acetic acid solution containing 2% by weight chitosan.

When acidic aqueous solution is added to the chitosan-silver gel, a solution results that can be used, for example, as a finish. A solid form of the complex can be produced from the gel by a method comprising the following steps:

(i) adding water to the gel, with stirring;
(ii) raising the pH to the product of step (i) to pH 7 to 8 by adding a basic solution as is commonly known in the art;
(iii) filtering the product of step (ii);
(iv) washing the filtered solids with water, then with acetonitrile;
(v) drying the washed solids under vacuum; and
(vi) optionally, grinding the dried product to a fine powder.

Typically, deionized water is used throughout and the pH is raised in step (ii) by dropwise addition of aqueous ammonium hydroxide or substituted ammonium hydroxide. The complex can then be added as a powder of desired particle size for the preparation of materials described herein.

As opposed to a heterogenous synthesis of chitosan-silver complex in which chitosan as an insoluble aqueous suspension is treated with a solution of silver nitrate (see, for example, "Characterization of Silver-binding Chitosan by Thermal Analysis and Electron Impact Mass Spectrometry," C. Peniche-Covas, M. S. Jimenez, A. Nunez, Carbohydrate Polymers (1988), 9, 249-256), the homogenous synthesis demonstrated here affords fibrous material with excellent swelling properties suitable for hydrogel applications, for example, as the absorbent element in a diaper, incontinence pad or garment, panty liner, tampon, or sanitary napkin.

In addition, the chitosan-silver complex powder can be reconstituted in aqueous solution and applied to a wide variety of surfaces, such as, but not limited to, polymers and ceramics. For example, chitosan-silver powder can be dissolved in 1-4% aqueous acetic acid solution to prepare 1-4% chitosan-silver solution that can be applied as a finish or the powder can be dissolved readily in 1-4% chitosan solution to give silver of desired concentration. The preferred surface comprises at least one naturally occurring or synthetic polymer, such as, but not limited to, those polymers described in commonly assigned U.S. patent application Ser. Nos. 10/288,762 and 10/919,844, U.S. Patent Application Publication No. 2003/0017194, and U.S. patent application Ser. No. 60/619,755 (filed Oct. 18, 2004, titled "Process for Making Antimicrobial Polymer Articles"), all of which are hereby incorporated by reference.

Examples of suitable naturally occurring polymers include but are not limited to cotton, wood, flax, shellac, silk, wool, natural rubber, leather, and mixtures thereof. Examples of suitable synthetic polymers include but are not limited to homopolymers, copolymers, mixtures, and blends of polyesters, polyetheresters, polyethers, polyamides, polyimides, polyetherimides, polyacetals, polystyrene, polyphenylene oxide, polyphenylene sulfide, polysulfones, poly (meth)acrylates, liquid crystalline polymers, polyetherketones, fluorine-containing polymers, acrylonitrile-styrene-butadiene resins, styrene-butadiene block copolymers, polycarbonates, cellulose-based polymers (e.g., cellulose, rayon, cellulose acetate), urea formaldehyde resins, polyacrylonitrile, epoxy resins, polyurethanes, melamine-formaldehyde resins, silicones, butyl rubber, polychloroprene, and polyolefins.

Blends of naturally occurring polymers and synthetic polymers are also contemplated. For example, wood pulp (WP)/polyester (PET) blends can contain 1-100% WP and 100-1% PET. Typical WP/PET blends include, for example, 55% pine WP/45% PET (2 oz/yd$^2$), 55% cedar WP/45% PET (1.5 oz/yd$^2$), 70% rayon/30% PET intimate fiber blend (8 mesh pattern, 2.2 oz/yd$^2$), 50% lyocell/50% PET intimate fiber blend (1.8 oz/yd$^2$), or 55% cedar WP/45% PET (2 oz/yd$^2$).

Examples of suitable polyolefins for use in the present invention are polypropylene, e.g., atactic polypropylene, isotactic polypropylene, syndiotactic polypropylene, biaxially oriented polypropylene (BOPP), metallocene-catalyzed polypropylene; polyethylene, e.g., high density polyethylene (HDPE), low density polyethylene (LDPE), linear low density polyethylene (LLDPE), metallocene-catalyzed polyethylene, very low density polyethylene (VLDPE), ultrahigh molecular weight polyethylene (UHMWPE), high performance polyethylene (HPPE); copolymers of ethylene and propylene; copolymers derived from ethylene or propylene and at least one monomer chosen from propylene, methyl acrylate, ethyl acrylate, n-butyl acrylate, methyl methacrylate, acrylic acid, methacrylic acid and carbon monoxide; and copolymers of olefins with a diolefin, such as a copolymer of ethylene, or of propylene, or of ethylene and other olefins, with: linear aliphatic nonconjugated dienes of at least six carbon atoms (such as 1,4-hexadiene) and other dienes, conjugated or not, such as norbornadiene, dicyclopentadiene, ethylidene norbornene, butadiene, and the like. Other suitable polymers are copolymers of ethylene and tetrafluoroethylene, such as Tefzel® ETFE fluoropolymer resin available from E. I. du Pont de Nemours & Co., Inc. (Wilmington, Del.).

Other polymers suitable for coating with the chitosan-silver complex solution are ionomers. The term "ionomer" as used herein refers to a polymer with inorganic salt groups attached to the polymer chain (Encyclopedia of Polymer Science and Technology, 2nd ed., H. F. Mark and J. I. Kroschwitz eds., vol. 8, pp. 393-396). Some examples of ionomers that have been commercialized are Surlyn® thermoplastic resin available from E. I. du Pont de Nemours & Co., Inc. (Wilmington, Del.) and Nafion® perfluorinated sulfonic acid membranes, also from DuPont. Polyesters and polyamides that have been polymerized with a low level of sulfonated comonomer to enhance textile dyeability (see, e.g., U.S. Pat. Nos. 5,559,205; 5,607,765; and 3,389,549) and sulfonated aromatic polyamides (see, e.g., U.S. Pat. Nos. 3,567,632 and 4,595,708) such as those used in reverse osmosis membranes and other selective separation membranes are also suitable substrates to be coated with the chitosan-silver complex solution.

The chitosan-silver powder retains its integrity over long storage periods, for example, more than a year of shell life without becoming extremely colored.

Fillers and Other Additives

Fillers useful in the present invention include, for example, alumina trihydrate (ATH), alumina monohydrate (AMH), Bayer hydrate (BayH), quartz and other forms of silica ($SiO_2$), magnesium hydroxide ($Mg(OH)_2$), calcium carbonate ($CaCO_3$), barium sulfate ($BaSO_4$) or decorative agents (e.g., mica, glass chips, clear acrylic chips, "color flop" pigments (pigments that change color as the angle of viewing changes)), as a list that is not exhaustive and not intended to limit the invention. Fillers can be present in amounts up to about 95% by weight. Typically, but not necessarily, the amount of filler is decreased by the weight percent of antimicrobial agent added.

Solid surface materials may also include functional or decorative additives such as pigments, dyes, flame retardant agents, parting agents, fluidizing agents, viscosity control agents, curing agents, antioxidants, and the like as may be known to those of ordinary skill in the art.

Uses

Solid Surface Materials

Solid surface materials of this invention are typically formed by casting into a sheet form or casting into a shape form such as a sink, for example. Solid surface materials of this invention can also be produced by, for example, compression molding, injection molding, extrusion, or vibro-compaction methods.

It is especially preferred that the solid surfaces of the present invention remain wet, damp or moist for optimum effectiveness. Examples of solid surfaces of the present invention include, but are not limited to, surfaces in home bathrooms, public restrooms, swimming pool areas, dormitories, stadiums, and athletic facilities: sinks, counter tops, shower walls and bases, and other walls that become wet during use. In medical care facilities, such as hospitals, clinics, medical vans, and nursing homes, the current invention provides antimicrobial protection in the form of surfaces for counter tops, sinks, shower walls and bases, and back splashes in, for example, patient rooms, laundry rooms, soiled linen areas, staff and visitor areas, intensive care and coronary care units.

The present invention is also useful for antimicrobial protection where there is indirect food contact with the solid surface. Some examples are: counter tops, sinks, back splashes, and table tops in kitchens; table tops, salad bar counters and shields, food lag areas, dirty dish areas, and dish washing and drying areas in restaurants and fast food establishments; certain areas in slaughterhouses where the nutrient insult is not excessive; table, counter top, and back splash areas in canning, freezing, red meat packing, and bread and pastry production facilities; and grocery and fresh food counter tops, displays, and other fixtures in a grocery store.

The present invention is also useful for the surfaces of writing instruments, such as pens and pencils, since pathogenic microorganisms are easily transmitted by hand contact, and perspiration would increase the antimicrobial efficacy.

Chitosan-Silver Complex

The chitosan-silver complex, which is dispersed in the solid surface materials of the present invention, can be used by itself to impart antimicrobial and antiodor functionality in a wide variety of applications. For example, a reconstituted solution of the chitosan-silver complex can be used as a finish solution for textiles applications as is commonly performed in the art.

Typically, a solution of the complex would be applied to an article's surface by any convenient means, such as but not limited to dipping, padding, or spraying, in a batch or continuous mode.

Articles comprising polymeric material treated with the chitosan-silver complex may be in the form of or comprise a film, membrane, laminate, knit fabric, woven fabric, nonwoven fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, or spinning.

Such articles include packaging for food, personal care (health and hygiene) items, and cosmetics. By "packaging" is meant either an entire package or a component of a package. Examples of packaging components include, but are not limited, to packaging film, liners, absorbent pads packaging, shrink bags, shrink wrap, trays, tray/container assemblies, caps, adhesives, lids, and applicators. Such absorbent pads, shrink bags, shrink wrap, and trays of the present invention are particularly useful for packaging meat, poultry, and fish.

The package may be in any form appropriate for the particular application, such as a can, box, bottle, jar, bag, cosmetics package, or closed-ended tube. The packaging may be fashioned by any means known in the art, such as by extrusion, coextrusion, thermoforming, injection molding, lamination, or blow molding.

Some specific examples of packaging include, but are not limited to, bottles, tips, applicators, and caps for prescription and non-prescription capsules and pills; solutions, creams, lotions, powders, shampoos, conditioners, deodorants, antiperspirants, and suspensions for eye, ear, nose, throat, vaginal, urinary tract, rectal, skin, and hair contact; lip product packaging; and caps.

Examples of applicators include lipstick, chapstick, and gloss; packages and applicators for eye cosmetics, such as mascara, eyeliner, shadow, dusting powder, bath powder, blusher, foundation and creams; and pump dispensers and components thereof. These applicators are used to apply substances onto the various surfaces of the body, and reduction of bacterial growth will be beneficial in such applications.

Other suitable forms of packaging components include drink bottle necks, replaceable caps, non-replaceable caps, and dispensing systems; food and beverage delivery systems; inhalers in pharmaceutical applications; baby bottle nipples and caps; and pacifiers. Where a liquid, solution or suspension is intended to be applied, the package may be fashioned for application in a form for dispensing discrete drops or for spraying of droplets.

Examples of end-use applications, other than packaging, in the area of food handling and processing that benefit from antimicrobial functionality and wherein microbial growth is reduced in the particular end-use of the consumer are coatings for components of food handling and processing equipment, such as temporary or permanent food preparation surfaces; conveyer belt assemblies and their components; equipment for mixing, grinding, crushing, rolling, pelletizing, and extruding and components thereof; heat exchangers and their components; drains and their components; equipment for transporting water such as, but not limited to, buckets, tanks, pipes, and tubing; and machines for food cutting and slicing and components thereof. Where the surface of such equipment components is metal, a coating of a polymer could first be applied to the metal surface. Alternatively, a film of such a polymer could be treated with a solution of chitosan-silver complex and then heat sealed to the equipment surface. In one embodiment, the equipment component is a screw for mixing and/or conveying that is an element in a single-screw or twin-screw extruder, such as, but not limited to, an extruder used for food processing; and the polymer coating comprises an ionomer.

Articles treated with a solution of the chitosan-silver complex can also be used in or as items of apparel, such as a swimsuit, undergarment, shoe component (for example, a woven or nonwoven shoe liner or insert), protective sports pad, child's garment, or medical garment (such as a gown, mask, glove, slipper, bootie, or head covering). Such garments particularly benefit from the inhibition of odor development.

Articles treated with a solution of the chitosan-silver complex can also be used in or as medical materials, devices, or implants, such as bandages, adhesives, gauze strips, gauze pads, medical or surgical drapes, syringe holders, catheters, sutures, IV tubing, IV bags, stents, guide wires, prostheses, orthopedic pins, dental materials, pacemakers, heart valves, artificial hearts, knee and hip joint implants, bone cements, vascular grafts, urinary catheter ostomy ports, orthopedic fixtures, pacemaker leads, defibrillator leads, ear canal shunts, cosmetic implants, ENT (ear, nose, throat) implants, staples, implantable pumps, hernia patches, plates, screws, blood bags, external blood pumps, fluid administration systems, heart-lung machines, dialysis equipment, artificial skin, ventricular assist devices, hearing aids, and dental implants.

In the hygiene area, articles that can be treated with a solution of the chitosan-silver complex include personal hygiene garments such as incontinence pads and garments, panty liners, sanitary napkins, sports pads, tampons and their applicators; and health care materials such as antimicrobial wipes, baby wipes, personal cleansing wipes, cosmetic wipes, diapers, medicated wipes or pads (for example, medicated wipes or pads that contain an antibiotic, a medication to treat acne, a medication to treat hemorrhoids, an anti-itch medication, an anti-inflammatory medication, or an antiseptic).

Articles that can be treated with a solution of the chitosan-silver complex also include items intended for oral contact, such as a baby bottle nipple, pacifier, orthodontic appliance or elastic bands for same, denture material, cup, drinking glass, toothbrush, or teething toy.

Additional child-oriented articles that benefit through treatment with a solution of the chitosan-silver complex include baby bottles, baby books, plastic scissors, toys, diaper pails, and a container to hold cleansing wipes.

Household articles that can be treated with a solution of the chitosan-silver complex include telephones and cellular phones; fiberfill, bedding, bed linens, window treatments, carpet, flooring components, foam padding such as mat and rug backings, upholstery components (including foam padding), nonwoven dryer sheets, laundry softener containing sheets, automotive wipes, household cleaning wipes, counter wipes, shower curtains, shower curtain liners, towels, washcloths, dust cloths, mops, table cloths, walls, and counter surfaces.

Treatment with a solution of the chitosan-silver complex is also useful in reducing or preventing biofilm growth on the surface of selective separation membranes (for example, pervaporation, dialysis, reverse osmosis, ultrafiltration, and microfiltration membranes), and air and water filters that comprise at least one polymer, for example, sulfonated aromatic polyamides.

Treatment with a solution of the chitosan-silver complex is also useful in providing an antifouling surface on boat components such as, but not limited to, boat hulls, boat parts, and boat motors. If the surface of the boat component does not comprise a polymer, for example, if the boat component had a metal surface, a coating of a polymer could first be applied to the boat component's surface. Alternatively, a polymeric film could be treated with the chitosan-silver complex and then heat sealed to the boat component's surface.

Devices used in fluid, e.g., water, transportation and/or storage can also benefit from the antimicrobial functionality imparted by application of the chitosan-silver complex. Exemplary devices include, but are not limited to, pipes and tanks. The inner surface, outer surface, or both surfaces of a pipe or tank can comprise an antifouling surface of the invention. If the surface(s) does not comprise a polymer, for example, if the pipe or tank had a metal surface, a coating of a polymer could first be applied to the surface. Alternatively, a film of such polymer could be treated with the chitosan-silver complex and then heat sealed to the surface(s).

In order to impart antimicrobial functionality to the products listed, the product can be treated with the chitosan-silver complex before it is manufactured, or after, or at any time during manufacture of the product. It is believed that the antimicrobial properties of the material will not change significantly.

EXAMPLES

Additional features of the invention are illustrated by the following Examples.

The meaning of abbreviations is as follows: "h" means hour(s), "min" means minute(s), "sec" means second(s), "d" means day(s), "µL" means microliter, "mL" means milliliters, "L" means liters, "µm" means micrometer, "ppm" means parts per million (i.e., milligrams per liter).

Testing Methods for Examples

The antimicrobial effectiveness of the various embodiments of this invention was evaluated by using the Antimicrobial Hard Surface Test Method and the Antimicrobial Hard Surface Wipe Test Method as described below:

Antimicrobial Hard Surface Test Method

The test is conducted using hard polymeric materials that are impregnated with an antimicrobial agent homogeneously dispersed throughout the entire thickness of the material (see U.S. Pat. No. 3,847,865 for Corian® material plaque preparation). Tiles of the test material are inoculated with a known density of microbial cells and incubated at controlled humidity to retard drying. Following standard microbiological techniques for enumerating microorganisms, significant efficacy is demonstrated when at least a 3-log reduction in cell density on test material compared to control material without antimicrobial agent is achieved.

The relationship between percent reduction and log reduction is conveniently seen by reference to the following:

TABLE 1

| Value | % Reduction |
|-------|-------------|
| 1 | 90 |
| 2 | 99 |
| 3 | 99.9 |
| 4 | 99.99 |
| 5 | 99.999 |

Procedure

1. In the chemical fume hood, buff/renew control and test Corian® 6×6 cm tiles by using either a maroon Scotch-Brite™ very fine abrasive pad (3M #7447) or 200 grit or finer sandpaper. In a biological safety cabinet, wipe each tile with an isopropanol wipe, place in a sterile deep petri plate (100×20 mm), air dry, and cover with the lid.

2. From an overnight culture grown in Trypticase Soy Broth (TSB) at 25° C., prepare inoculum that is approximately $1 \times 10^6$ cfu (colony forming units)/ml phosphate buffer*. (Typically an overnight culture is diluted 1:1,000 in phosphate buffer to yield this density.) Determine the final cell density by performing a serial-dilution spread plate count of the inoculum on Trypticase Soy Agar (TSA).

3. Inoculate each tile by placing 0.5 mL of inoculum on the surface and spreading evenly with a sterile glass or plastic spreader. The inoculum should not go over the edge of the tile, but should remain on the "test side". Put the lid on the petri plate and place in an open tray. Incubate in an environmental chamber at 25° C. and 85% relative humidity (% RH).

4. To determine speed of kill (i.e., time required to achieve a 3-log or 99.9% reduction) for the antimicrobial tiles, generate a time-curve by incubating for 1, 2, 3, 4, 6, and 8 h. After the designated incubation/exposure time, remove the petri plates from the environmental chamber. In the biological safety cabinet, remove the petri dish lid and rinse the tile twice with phosphate buffer using a sterile 5 mL pipet. Use 4.5 mL for the first rinse and 5.0 mL for the second rinse. It is critical to rinse the tile by repeatedly sucking and expelling the buffer as the pipet is moved across the entire tile test surface. After the last rinse, thoroughly wipe the surface with a sterile 1 inch square gauze pad. Place the gauze into a sterile test tube along with the buffer rinses.

5. Determine the bioburden of the rinse buffer using a phosphate buffer serial-dilution spread plate technique on TSA. Incubate the plates at the optimal growth temperature and conditions for the test microorganism for at least 24 h. Count the colonies on plates and calculate the density taking into account all dilutions. Report the findings as cfu/ml.

6. The Δt value may be calculated as follows: Δt=C−B, where Δt is the activity constant for contact time t, C is the mean $\log_{10}$ density of microbes rinsed off of control tiles after X hours of incubation, and B is the mean $\log_{10}$ density of microbes rinsed off of test tiles after X hours of incubation.

| *Stock Phosphate Buffer: | |
|---|---|
| Monobasic Potassium Phosphate | 22.4 g |
| Dibasic Potassium Phosphate | 56.0 g |
| Deionized Water | to 1000 mL |

Adjust to pH 6.0-7.0 with either NaOH of HCl, filter, sterilize, and store at 4° C. until use.

Working Phosphate Buffer:

Dilute 1 mL of stock phosphate buffer in 800 mL of sterile deionized water (pH should be 6.0-7.0), dispense in working volumes and autoclave.

Antimicrobial Hard Surface Wipe Test Method

Summary of Method

This test is used to determine the frequency of renewal required for an antimicrobial surface that can be regenerated by buffing with an abrasive pad or sandpaper. The experimental design described below can be used to determine the duration of antimicrobial efficacy under normal use conditions. A surface with "reduced activity" is one in which the antimicrobial activity has fallen below a 3-log reduction capability.

Wiping with Damp Cloth: Soapy Water

The purpose of this protocol is to determine the effect of repeated typical clean-ups with soapy water on the durability of the efficacy of antimicrobial surfaces.

1. Prepare a set of control and test tiles as described in the "Antimicrobial Hard Surface Test Method".
2. Wipe each tile set with a sterile cloth (e.g. cheesecloth, typical cotton kitchen towel, sponge, pre-moistened wipe, etc.) dampened with soapy water. The preparation of the soapy water is per the soap manufacturer's label instructions. Completely soak the cloth in the soapy water and hand wring prior to each use. A back and forth motion is used to completely wipe the surface of each tile.
3. After each wipe, rinse the tile with sterile deionized water to remove any soap residue and air dry.
4. After each set of 50 wipes, test the control and test tiles for antimicrobial efficacy using the "Antimicrobial Hard Surface Test Method".
5. Continue test in sets of 50 wipes until either an expected use period is satisfied or until the antimicrobial surface shows reduced activity. When Δt<3.0, the test tile is considered to have reduced activity.

Wiping with Damp Cloth: Liquid or Spray Disinfectant/Sanitizer

The purpose of this protocol is to determine the effect of repeated typical clean-ups with liquid disinfectants or sanitizers on the durability of the efficacy of antimicrobial surfaces.

1. Prepare a set of control and test tiles as described in the "Antimicrobial Hard Surface Test Method".
2. Manufacturers use directions for each disinfectant/sanitizer are not consistent. In order to standardize the exposure conditions, use the following directions. For liquid products, completely soak a sterile cloth in the disinfectant/sanitizer solution prepared according to the manufacturer's label directions and hand wring prior to each use. Wipe each tile with a back and forth motion to completely cover the surface of each tile. For spray products, spray the tile surface twice to ensure a thorough wetting and wipe once using a back and forth motion with a sterile cloth.
3. After each set of 50 wipes, test the control and test tiles for antimicrobial efficacy using the "Antimicrobial Hard Surface Test Method".
4. Continue test in sets of 50 wipes until either an expected use period is satisfied or until the antimicrobial surface shows reduced activity. When Δt<3.0, the test tile is considered to have reduced activity.

Shake Flask Test for Antimicrobial Testing of Materials

The following procedure was used to test the nonwoven samples in Example 9 for antimicrobial activity:

1. Inoculate a single, isolated colony from a bacterial or yeast agar plate culture in 15-25 ml of Trypticase Soy Broth (TSB) in a sterile flask. Incubate at 25-37° C. (use optimal growth temperature for specific microbe) for 16-24 h with or without shaking (select appropriate aeration of specific strain). For filamentous fungi, prepare sporulating cultures on agar plates.
2. Dilute the overnight bacterial or yeast culture into sterile phosphate buffer (see below) at pH 6.0 to 7.0 to obtain approximately $10^5$ colony forming units per ml (cfu/ml). The total volume of phosphate buffer needed will be 50 ml×number of test flasks (including controls). For filamentous fungi, prepare spore suspensions at $10^5$ spores/ml. Spore suspensions are prepared by gently resuspending spores from an agar plate culture that has been flooded with sterile saline or phosphate buffer. To obtain initial inoculum counts, plate final dilutions (prepared in phosphate buffer) of $10^{-4}$ and $10^{-3}$ onto Trypticase Soy Agar (TSA) plates in duplicate. Incubate plates at 25-37° C. overnight.
3. Transfer 50 ml of inoculated phosphate buffer into each sterile test flask containing 0.5 g of material to be tested. Also, prepare control flasks of inoculated phosphate buffer and uninoculated phosphate buffer with no test materials.
4. Place all flasks on a wrist-action shaker and incubate with vigorous shaking at room temperature. Sample all flasks periodically and plate appropriate dilutions onto TSA plates. Incubate at 25 to 37° C. for 16 to 48 h and count colonies.
5. Report colony counts as the number of Colony Forming Units per ml (cfu/ml).
6. The Δt value may be calculated as follows: Δt=C−B, where Δt is the activity constant for contact time t, C is the mean $\log_{10}$ density of microbes in flasks of untreated control materials after X hours of incubation, and B is the mean $\log_{10}$ density of microbes in flasks of treated materials after X hours of incubation. Δt is typically calculated at 4, 6, or 24 hours and may be expressed as $\Delta t_x$.

| Stock phosphate buffer: | |
|---|---|
| Monobasic Potassium Phosphate: | 22.4 g |
| Dibasic Potassium Phosphate: | 56.0 g |
| Deionized Water: | Bring up volume to 1000 ml |

Adjust the pH of the phosphate buffer to pH 6.0 to 7.0 with either NaOH or HCl, filter, sterilize, and store at 4° C.

until use. The working phosphate buffer is prepared by diluting 1 ml of stock phosphate buffer in 800 ml of sterile deionized water.

Example 1

Preparation of Chitosan-Silver Nitrate Complexes

Chitosan (42 g, ChitoClear® food grade chitosan, Primex, Iceland) was dissolved in 2% aqueous acetic solution (1100 mL) and stirred vigorously. A solution of silver nitrate (30 g) in deionized water (100 mL) was added over a period of 10 min. A clear, thick gel resulted. Additional water (300 mL) was added to the gel and stirred for 30 min. Concentrated ammonium hydroxide was added in drops to raise pH to 7-8. The product was filtered, washed with water (4×500 mL), and then with acetonitrile (4×500 mL). The resulting product was dried under vacuum for two days, ground to a fine powder, and used as such in the Corian® AB™ material preparation. Yield of the product was 53.7 g. The amount of silver in the complex was determined by Inductively Coupled Plasma spectroscopy (ICP), which is an atomic emission spectroscopy method in which inductively coupled plasmas are used as the excitation source (see, for example, *Inductively Coupled Plasma Emission Spectroscopy, pt.* 1, P. W. J. M. Boumans, John Wiley & Sons (New York, N.Y.), 1987, pp. 2-3). ICP silver metal analysis of this material indicated the proportion of silver to be 13.5% by weight.

In contrast, when a chitosan/silver complex was prepared by treating a suspension of chitosan with silver nitrate solution, the resultant product visually appeared the same as the starting material, did not form a gel, and had not dissolved in deionized water even after two days. The absence of swelling of this preparation clearly indicates the lack of cross linking of chitosan chain by silver and it is likely that the metal is distributed more on the surface of the chitosan than dispersed within it.

Example 2

Preparation of Chitosan-Silver Nitrate Complexes with Varying Silver Content

Five solutions of chitosan (20 g each, ChitoClear®, Primex, Iceland) in 500 mL of water containing 7.5 mL of acetic acid were treated successively with aqueous solutions (50 mL) of silver nitrate in the following proportions. Solution A in 7.2 g, B=3.6 g, C=1.8 g, D=0.9 g, E=0.45 g of silver nitrate. The reaction was conducted and processed as described in the previous Example. Yield of the products 1A through 1E ranged from 25 to 30.0 g.

Silver Content by ICP Analysis:
1A=10.5% silver
1B=9.5% silver
1C=5.1% silver
1D=2.2% silver
1E=1.6% silver In the following Examples 3-5, Corian® material plaques, 6 cm by 6 cm by about 1.3 cm, containing additives as indicated, were prepared according to U.S. Pat. No. 3,847,865.

Example 3

In the first plaque preparation, plain chitosan powder (ChitoClear®, Primex, Iceland) in 0.5%, 1.0%, and 3% concentrations by weight were added to the Corian® material mix and cast into plaques. As shown in FIG. 1, no significant antimicrobial activity was observed for these samples.

Example 4

Figure 2:
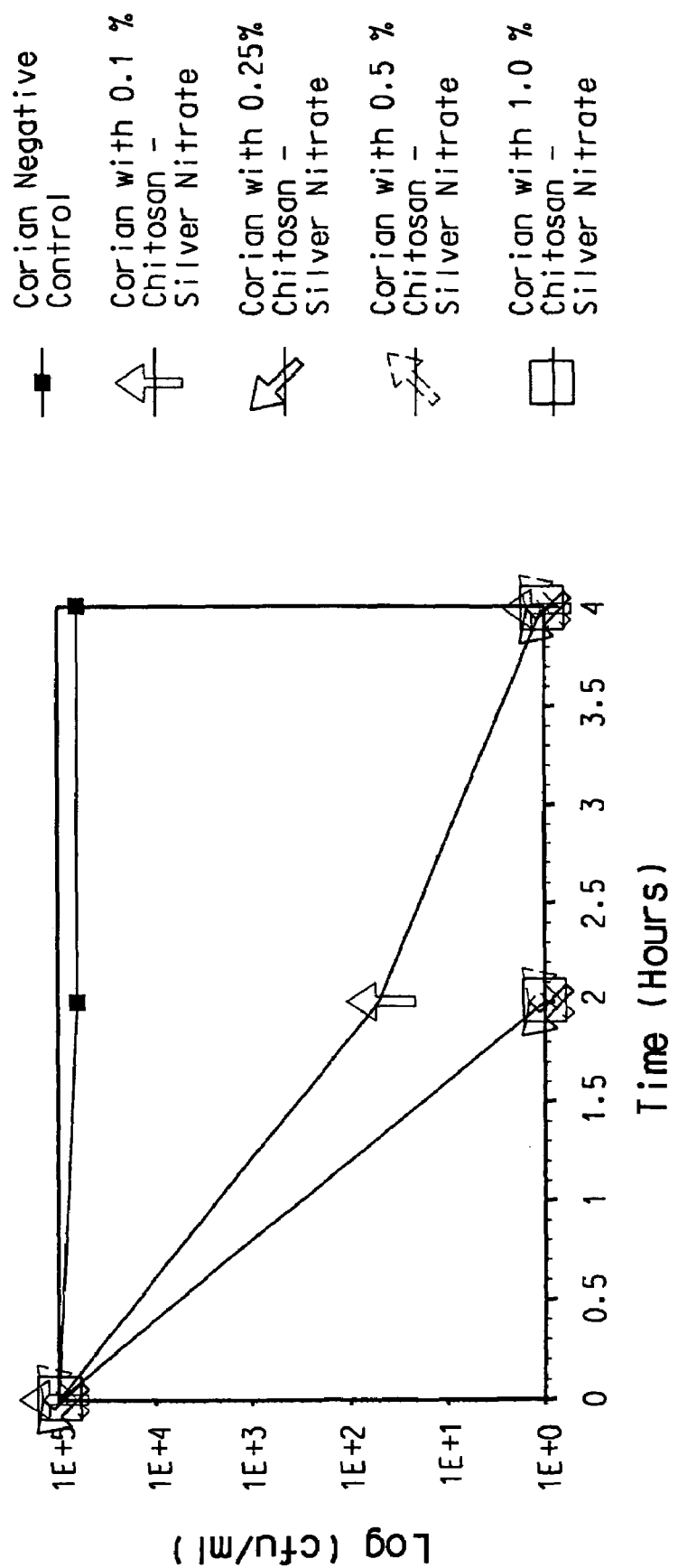
FIG. 2 shows the results of Corian® material with 0.1%, 0.25%, 0.5%, and 1.0% chitosan-silver nitrate content vs. *Escherichia coli* (ATCC 25922).
Figure 3:
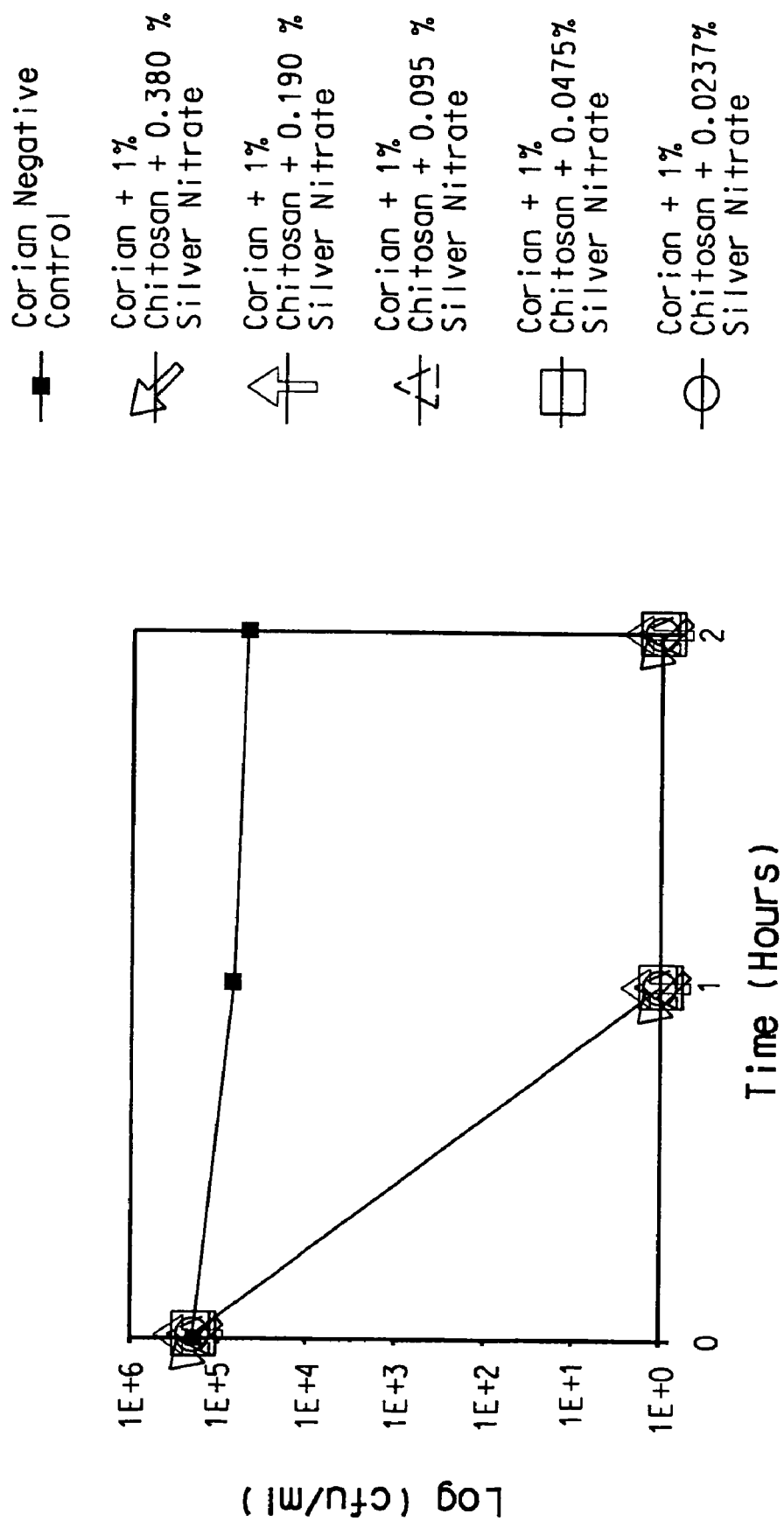
FIG. 3 shows the results of Corian® material with 1% chitosan and 0.0237%, 0.0475%, 0.095%, 0.190% and 0.380% silver nitrate content vs. *Escherichia coli* (ATCC 25922). The respective chitosan to silver ratios as determined by ICP analysis are 1:0.016, 1:0.022, 1:0.05, 1:0.095, and 1:0.105.
Figure 4:
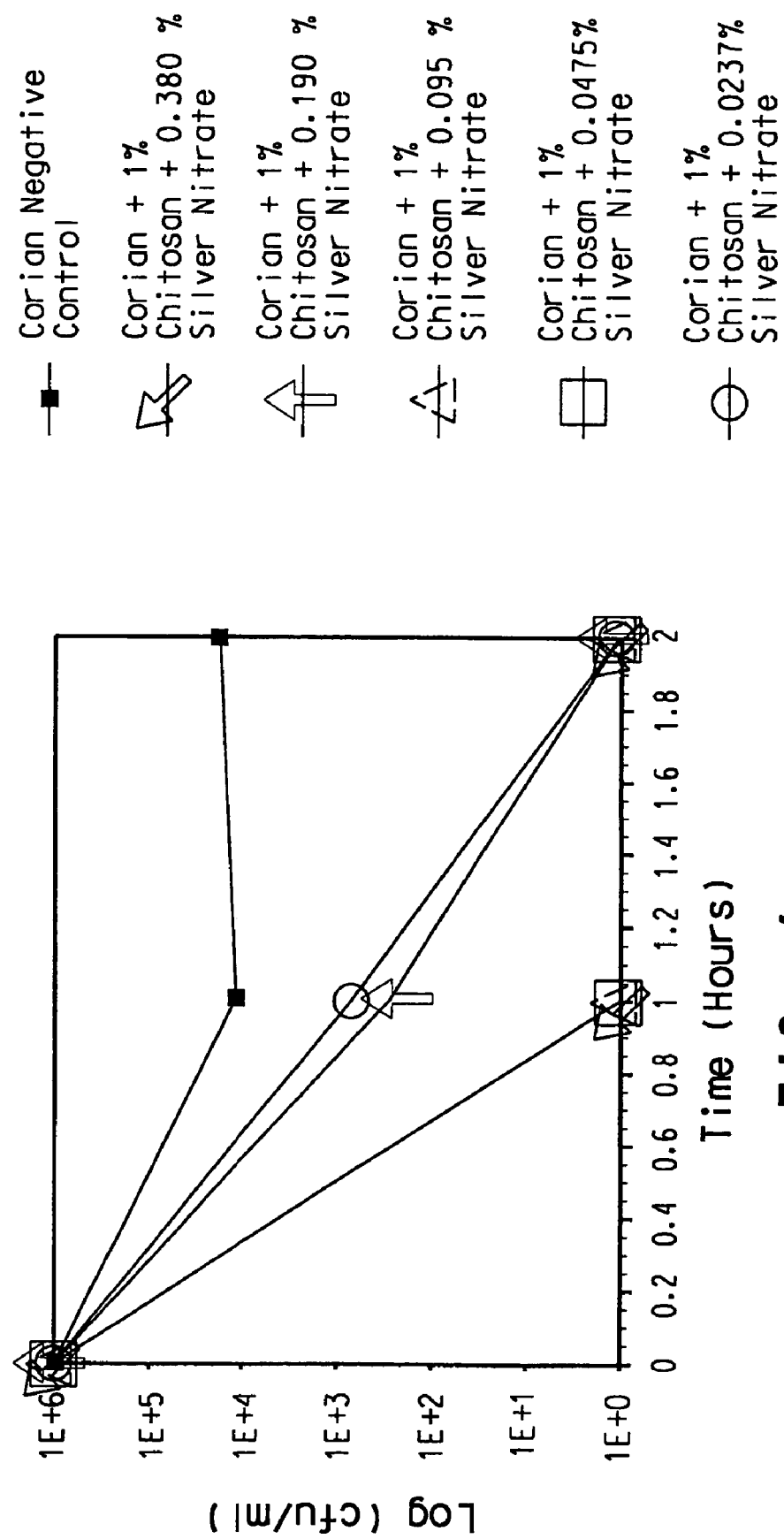
FIG. 4 shows the results of Corian® material with 1% chitosan and 0.0237%, 0.0475%, 0.095%, 0.190%, and 0.380% silver nitrate content vs. *Listeria weshimeri* (ATCC 35897). The respective chitosan to silver ratios as determined by ICP analysis are 1:0.016, 1:0.022, 1:0.05, 1:0.095, and 1:0.105.
Figure 5:
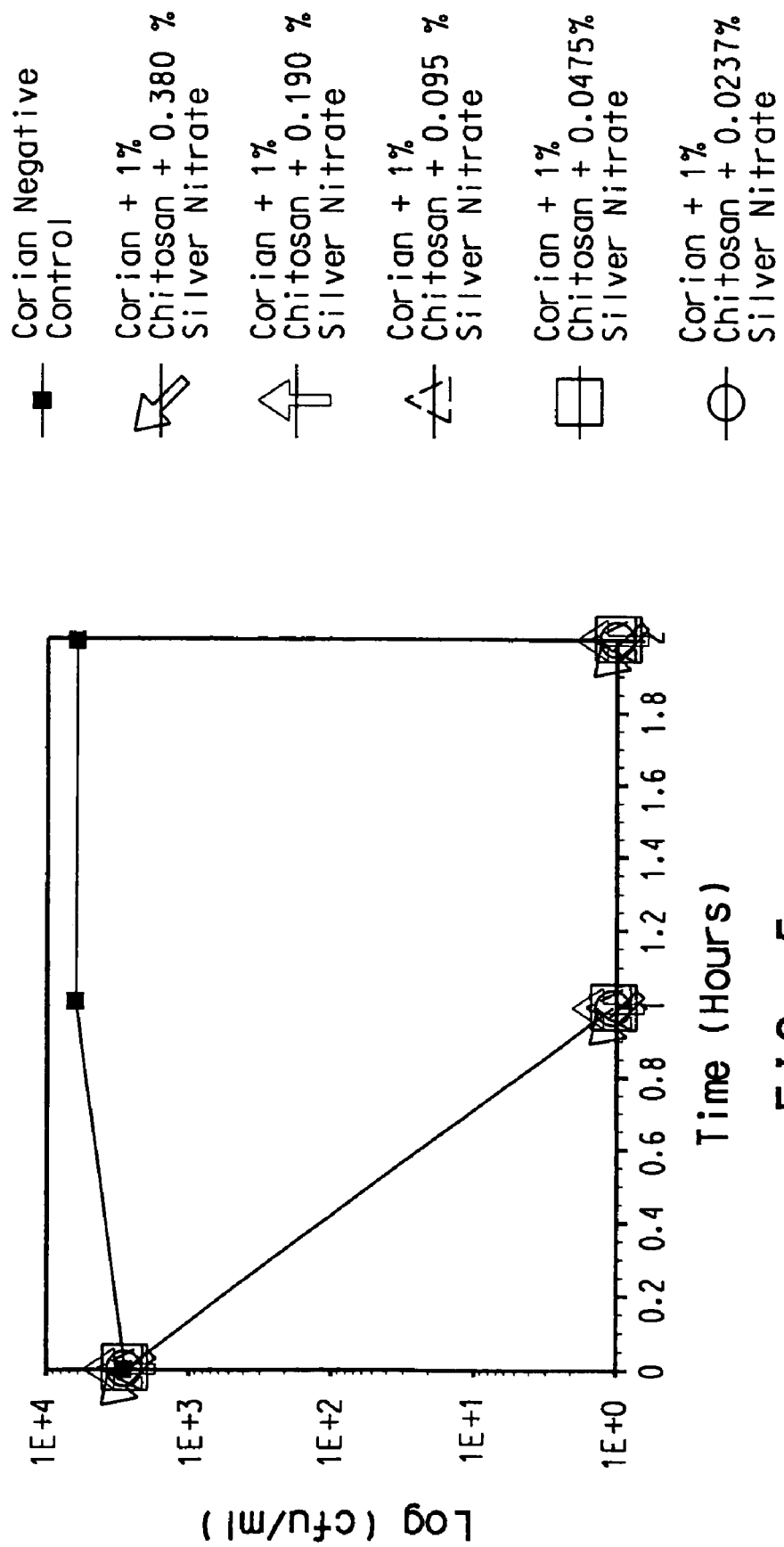
FIG. 5 shows the results of Corian® material with 1% chitosan and 0.0237%, 0.0475%, 0.095%, 0.190%, and 0.380% silver nitrate content vs. *Candida albicans* (ATCC 10231). The respective chitosan to silver ratios as determined by ICP analysis are 1:0.016, 1:0.022, 1:0.05, 1:0.095, and 1:0.105.
Figure 6:
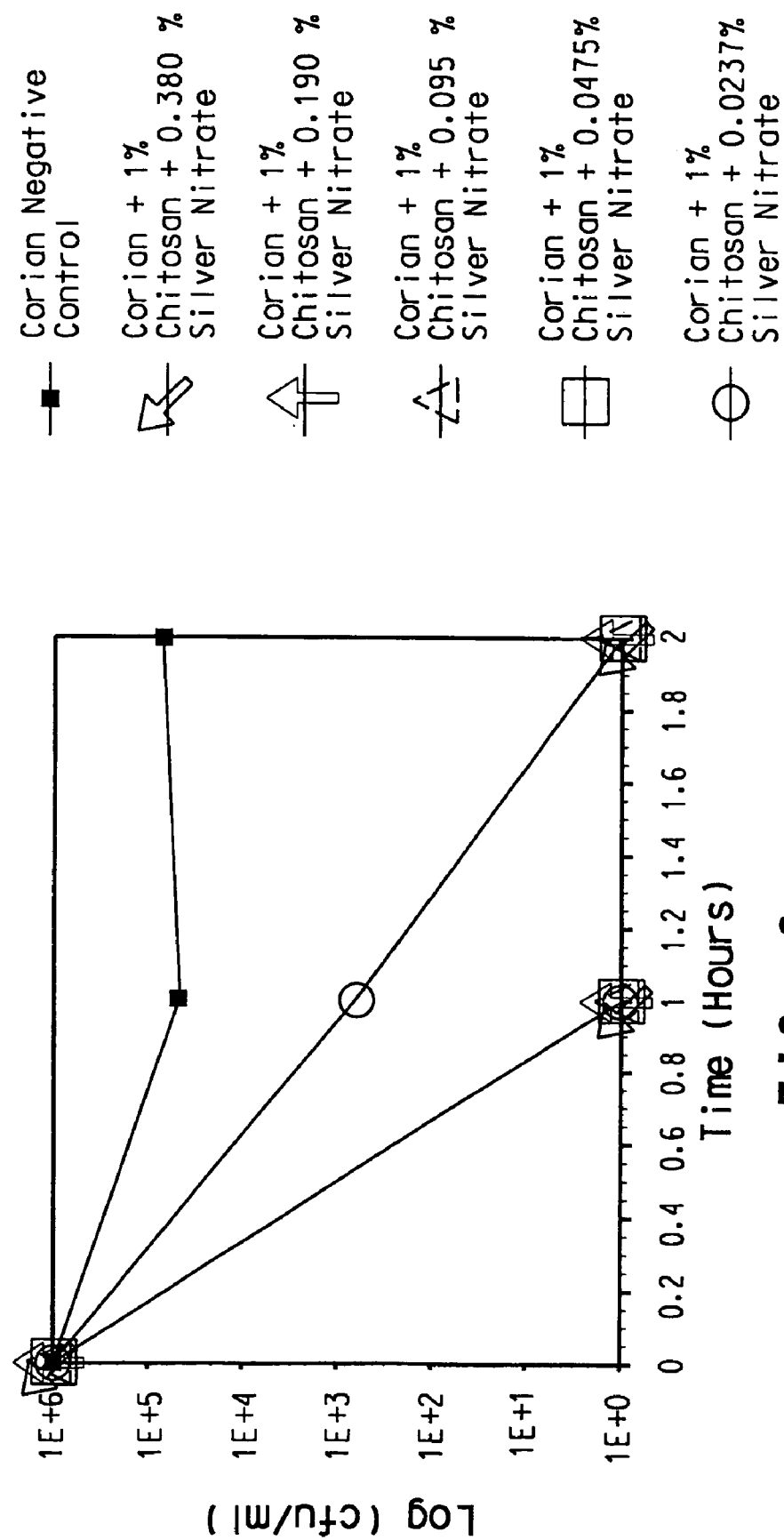
FIG. 6 shows the results of Corian® material with 1% chitosan and 0.0237%, 0.0475%, 0.095%, 0.190%, and 0.380% silver nitrate content vs. *Staphylococcus aureus* (ATCC 6538). The respective chitosan to silver ratios as determined by ICP analysis are 1:0.016, 1:0.022, 1:0.05, 1:0.095, and 1:0.105.
Figure 7:
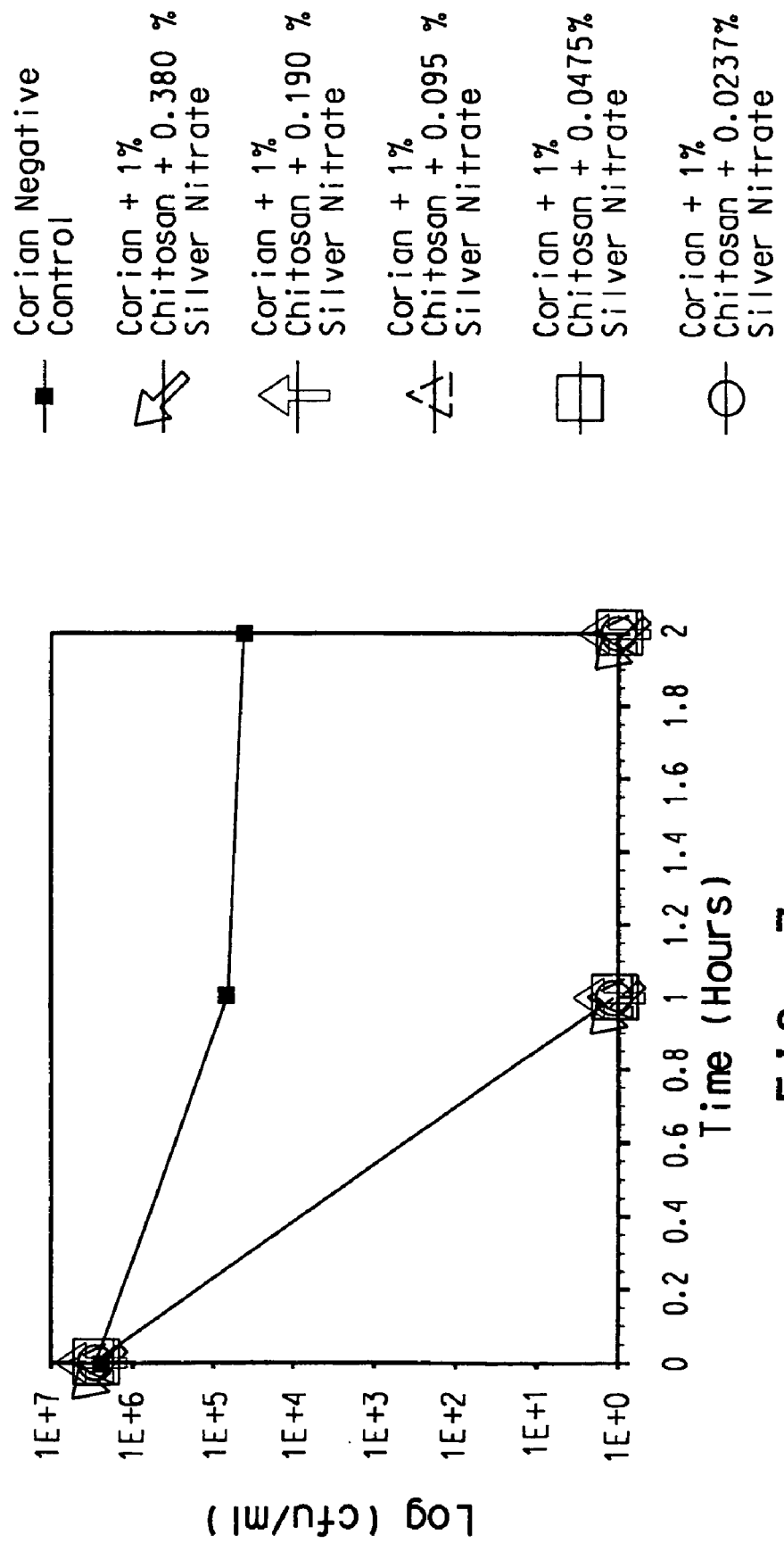
FIG. 7 shows the results of Corian® material with 1% chitosan and 0.0237%, 0.0475%, 0.095%, 0.190%, and 0.380% silver nitrate content vs. *Escherichia coli* (O157: H7). The respective chitosan to silver ratios as determined by ICP analysis are 1:0.016, 1:0.022, 1:0.05, 1:0.095, and 1:0.105.
Figure 8:
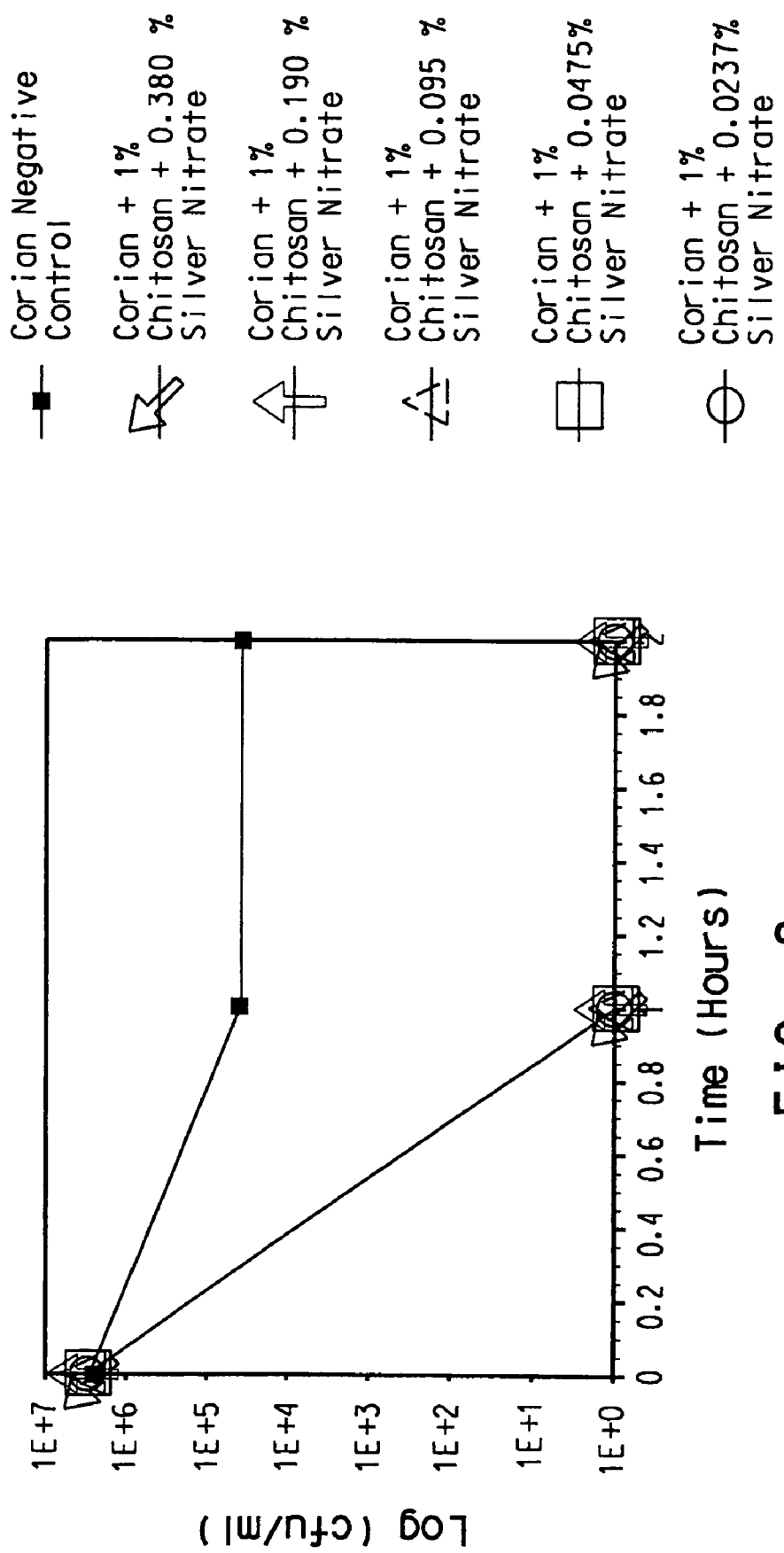
FIG. 8 shows the results of Corian® material with 1% chitosan and 0.0237%, 0.0475%, 0.095%, 0.190%, and 0.380% silver nitrate content vs. *Klebsiella pneumoniae* (ATCC 4352). The respective chitosan to silver ratios as determined by ICP analysis are 1:0.016, 1:0.022, 1:0.05, 1:0.095, and 1:0.105.
Figure 9:
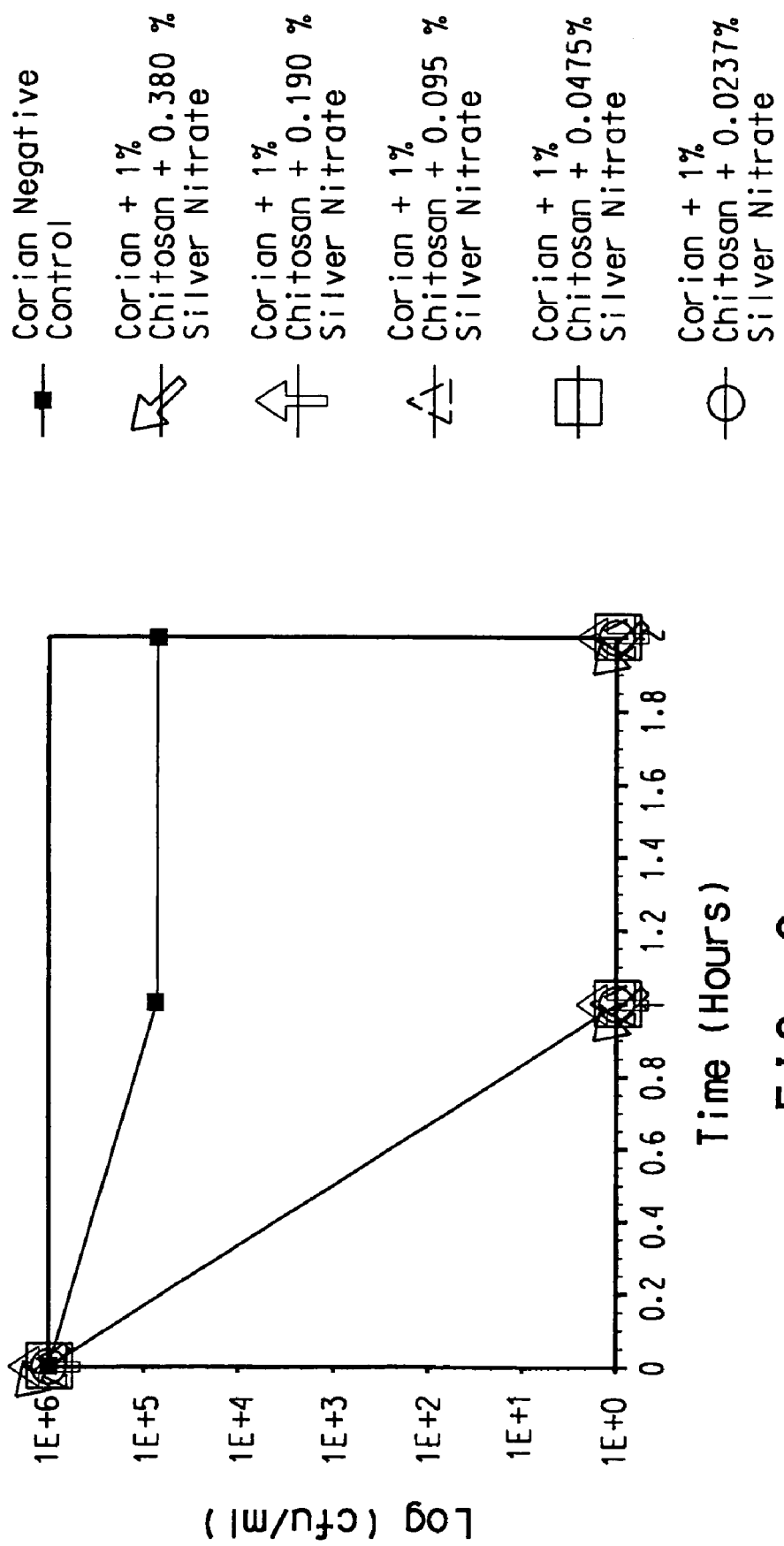
FIG. 9 shows the results of Corian® material with 1% chitosan and 0.0237%, 0.0475%, 0.095%, 0.190%, and 0.380% silver nitrate content vs. *Salmonella cholerasuis* (ATCC 9239). The respective chitosan to silver ratios as determined by ICP analysis are 1:0.016, 1:0.022, 1:0.05, 1:0.095, and 1:0.105.

Chitosan-silver nitrate powder from Example 1 was added to the plaque mixtures in 0.1%, 0.25%, 0.5%, and 1.0% concentrations by weight. The effective concentrations of the silver in these samples based on the additives were 0.01%, 0.03%, and 0.13%, respectively. These plaques exhibited effective antimicrobial activity as shown in FIG. 2.

Example 5

The following five Corian® material plaques were made as described in Example 4, except the chitosan concentration in all of these preparations was maintained at 1% by weight and the amount of silver nitrate relative to chitosan was changed using the material described in Example 2. Thus, the amounts of chitosan-silver in samples A to E respectively, were: 1:0.105; 1:0.095; 1:0.05; 1:0.022; 1:0.016. All these plaques exhibited bactericidal activity against a variety of organisms as shown in FIGS. 3 through 9.

Figure 10:
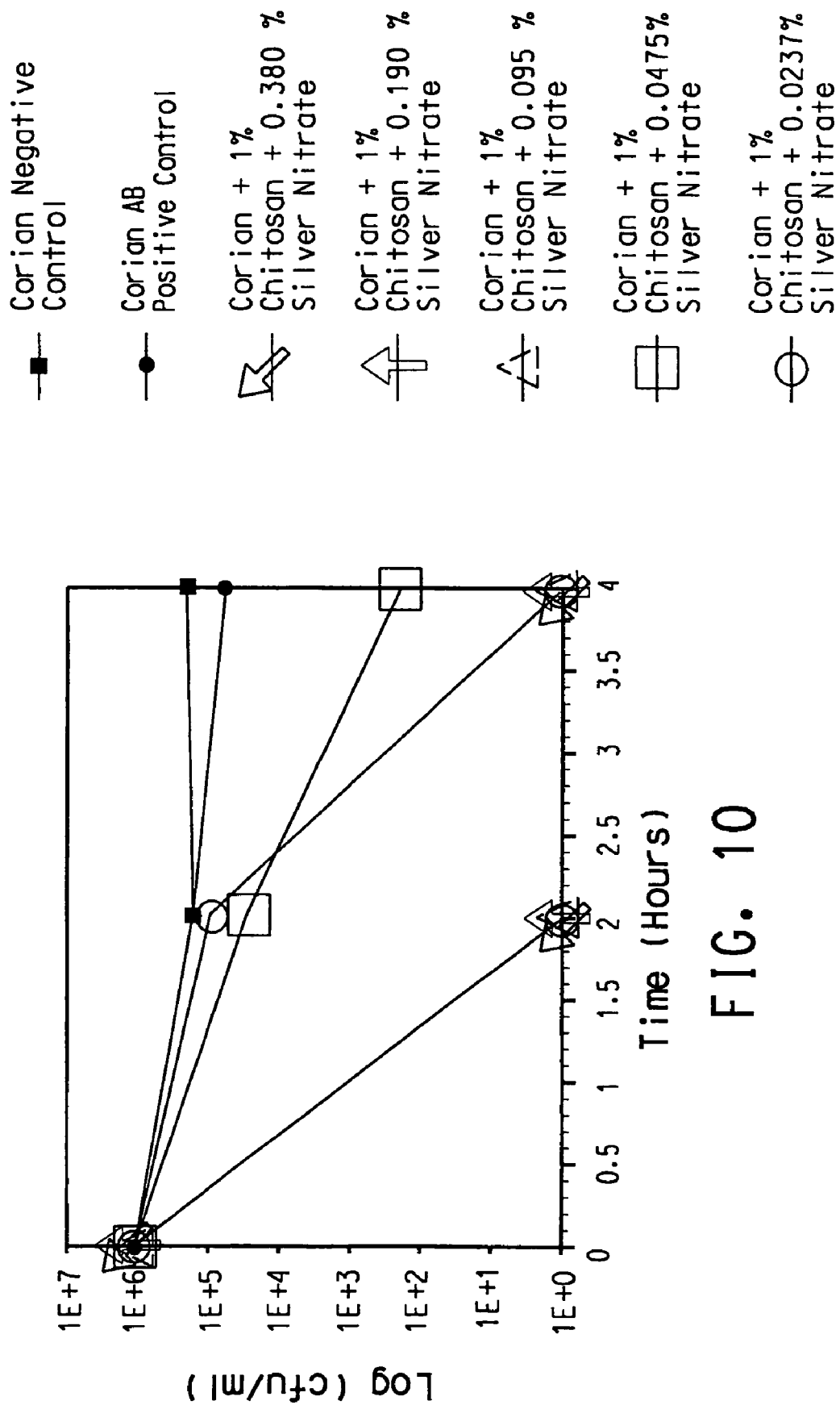
FIG. 10 shows the results of Corian® material with 1% chitosan and 0.0237%, 0.0475%, 0.095%, 0.190%, and 0.380% silver nitrate content vs. *Escherichia coli* (O157:H7) in the presence of BSA. The respective chitosan to silver ratios as determined by ICP analysis are 1:0.016, 1:0.022, 1:0.05, 1:0.095, and 1:0.105. Corian® AB™ material is an antimicrobial Corian® material containing silver zirconium phosphate and is used in this experiment as a putative positive control. The silver zirconium phosphate active was rendered inactive against this bacterium in the presence of BSA.
Figure 11:
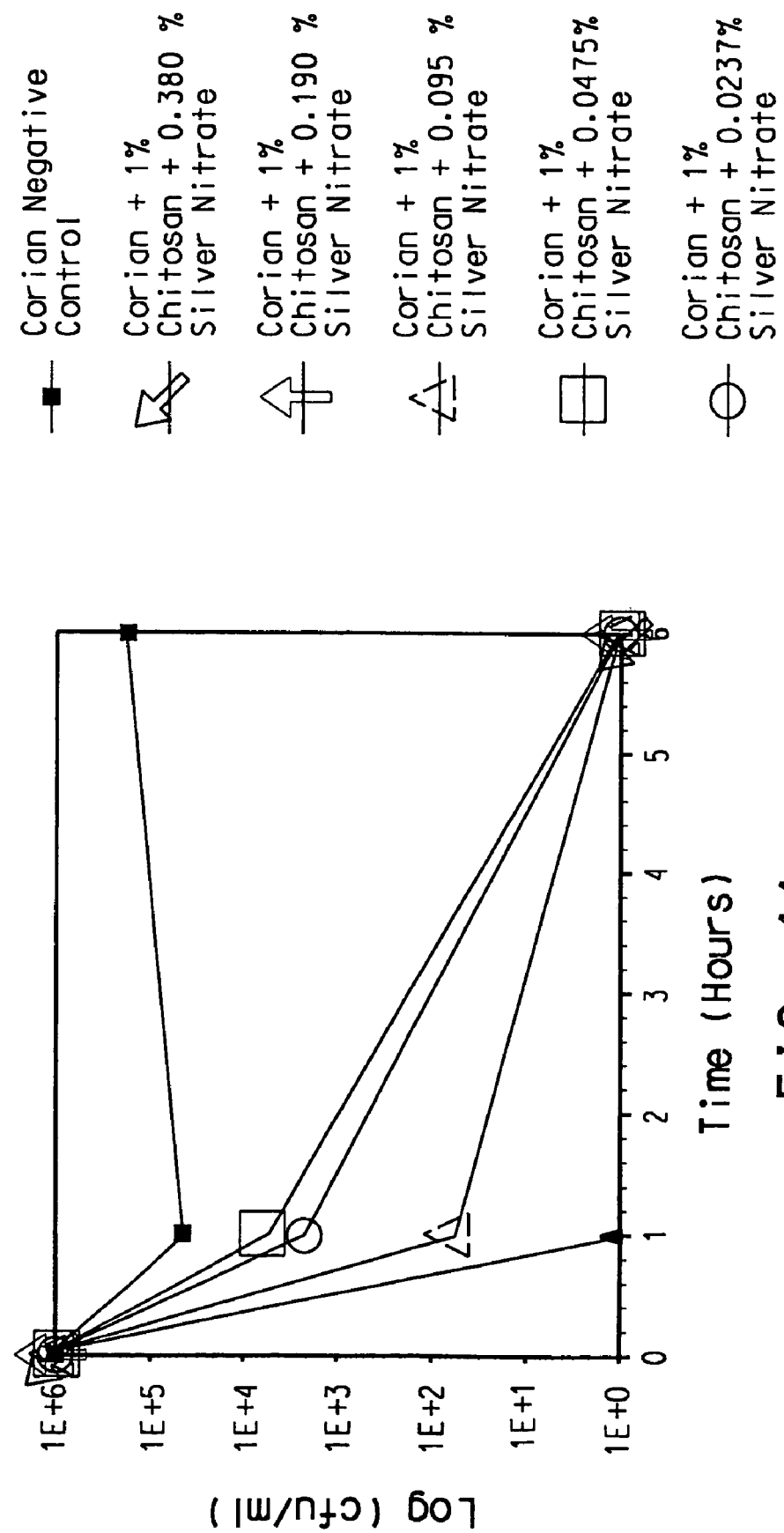
FIG. 11 shows the results of Corian(® material with 1% chitosan and 0.0237%, 0.0475%, 0.095%, 0.190%, and 0.380% silver nitrate content vs. *Escherichia coli* (ATCC 25922) in the presence of BSA. The respective chitosan to silver ratios as determined by ICP analysis are 1:0.016, 1:0.022, 1:0.05, 1:0.095, and 1:0.105.

In addition, these chitosan-silver Corian® material plaques maintained antimicrobial activity against *Escherichia coli* O157:H7 (FIG. 10), a microbe that is difficult to kill, and against *Escherichia coli* ATCC 25922 (FIG. 11) in the presence of "soil". Bovine serum albumin (BSA) was added at 1.15 g per liter of phosphate buffer and utilized to prepare the inoculum as described for the "Antimicrobial Hard Surface Test Method". This is a significant finding since many antimicrobial surfaces are inactivated in the presence of "soil", as can be seen with the Corian®AB™ material positive control that was rendered ineffective against *E. coli* O157:H7 (FIG. 10).

Example 6

Figure 12:
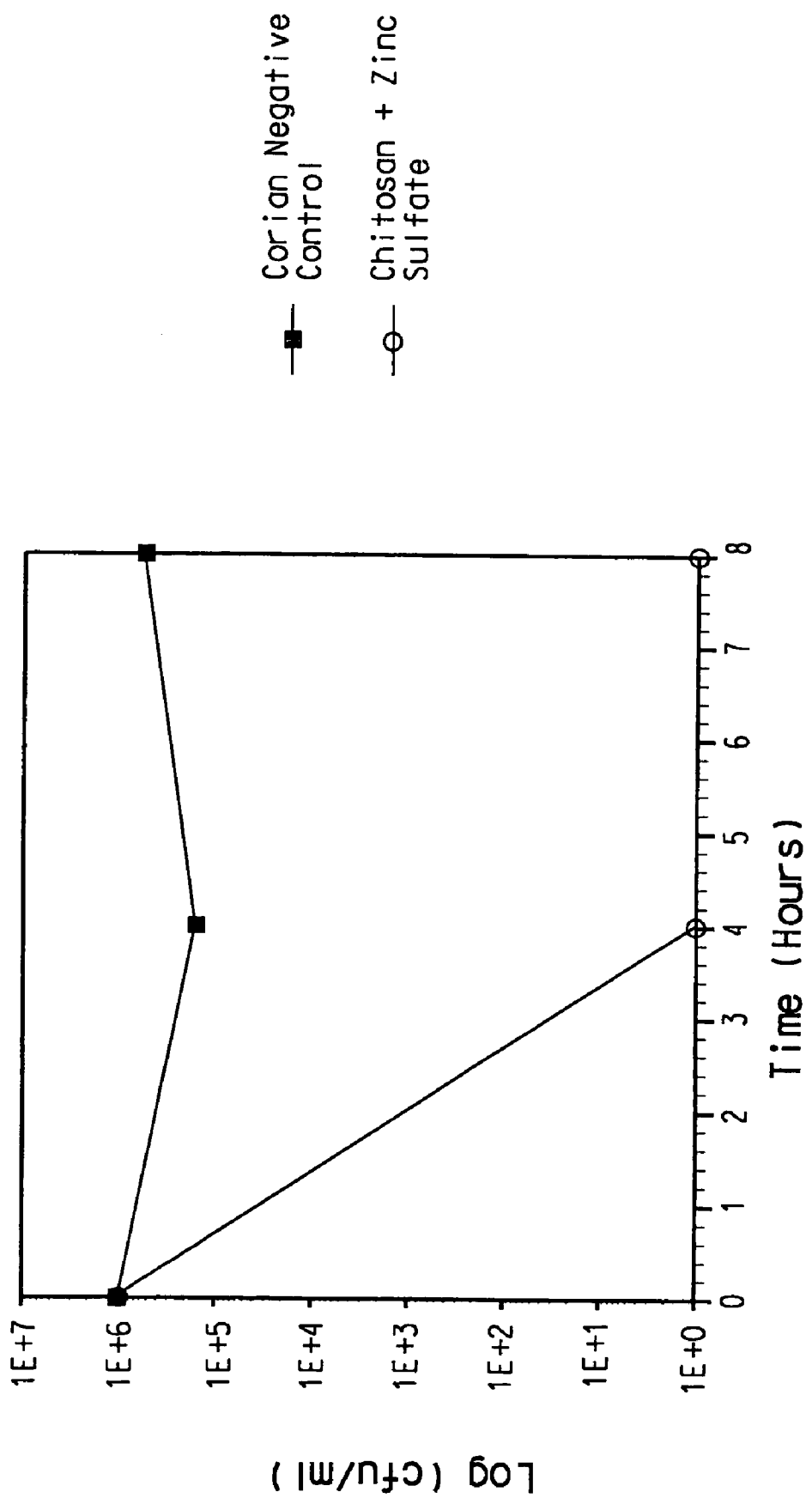
FIG. 12 shows the results of Corian® material with chitosan-zinc sulfate vs. *Escherichia coli* (ATCC 25922).
Figure 13:
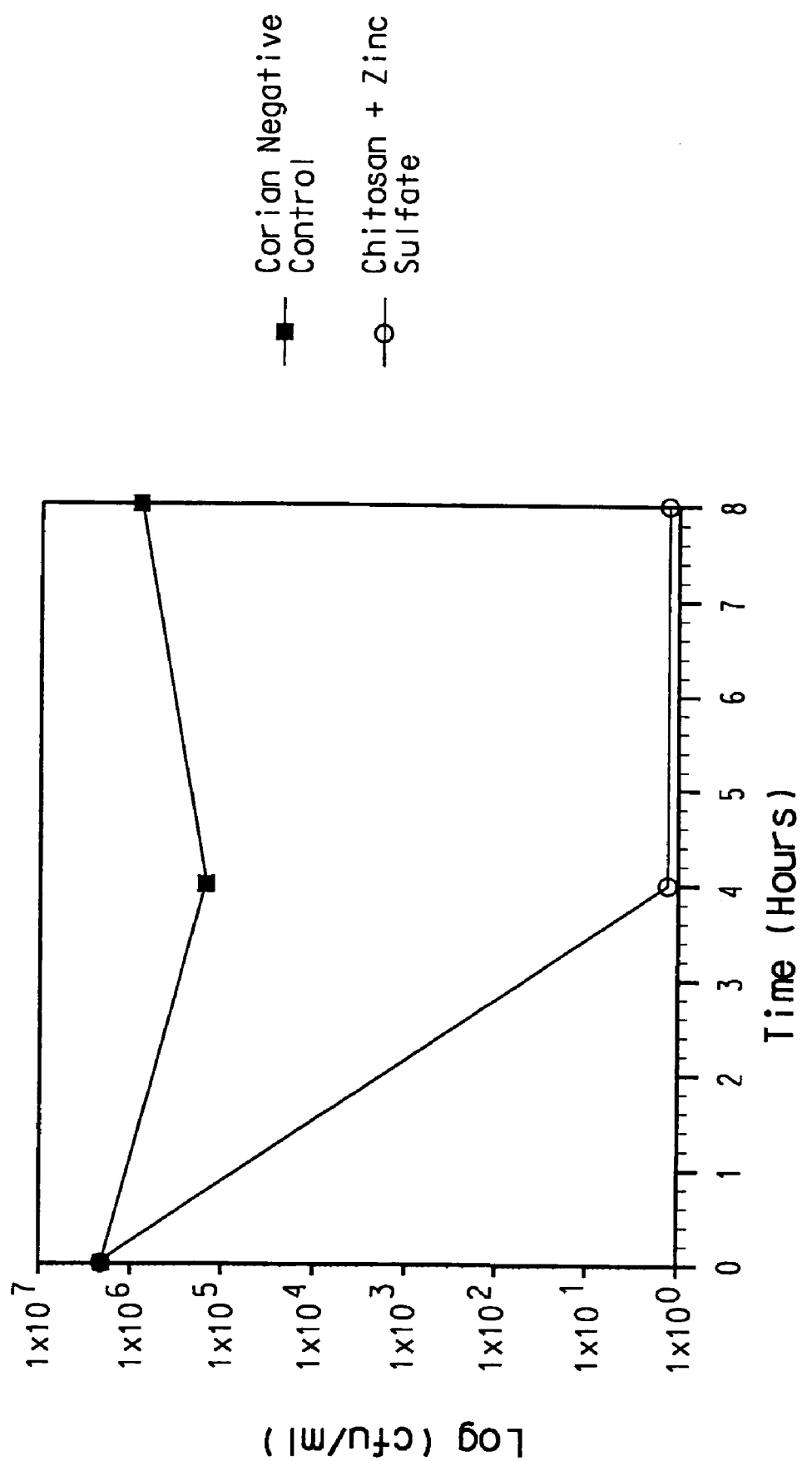
FIG. 13 shows the results of Corian® material with chitosan-zinc sulfate vs. *Staphylococcus aureus* (ATCC 6538).
Figure 14:
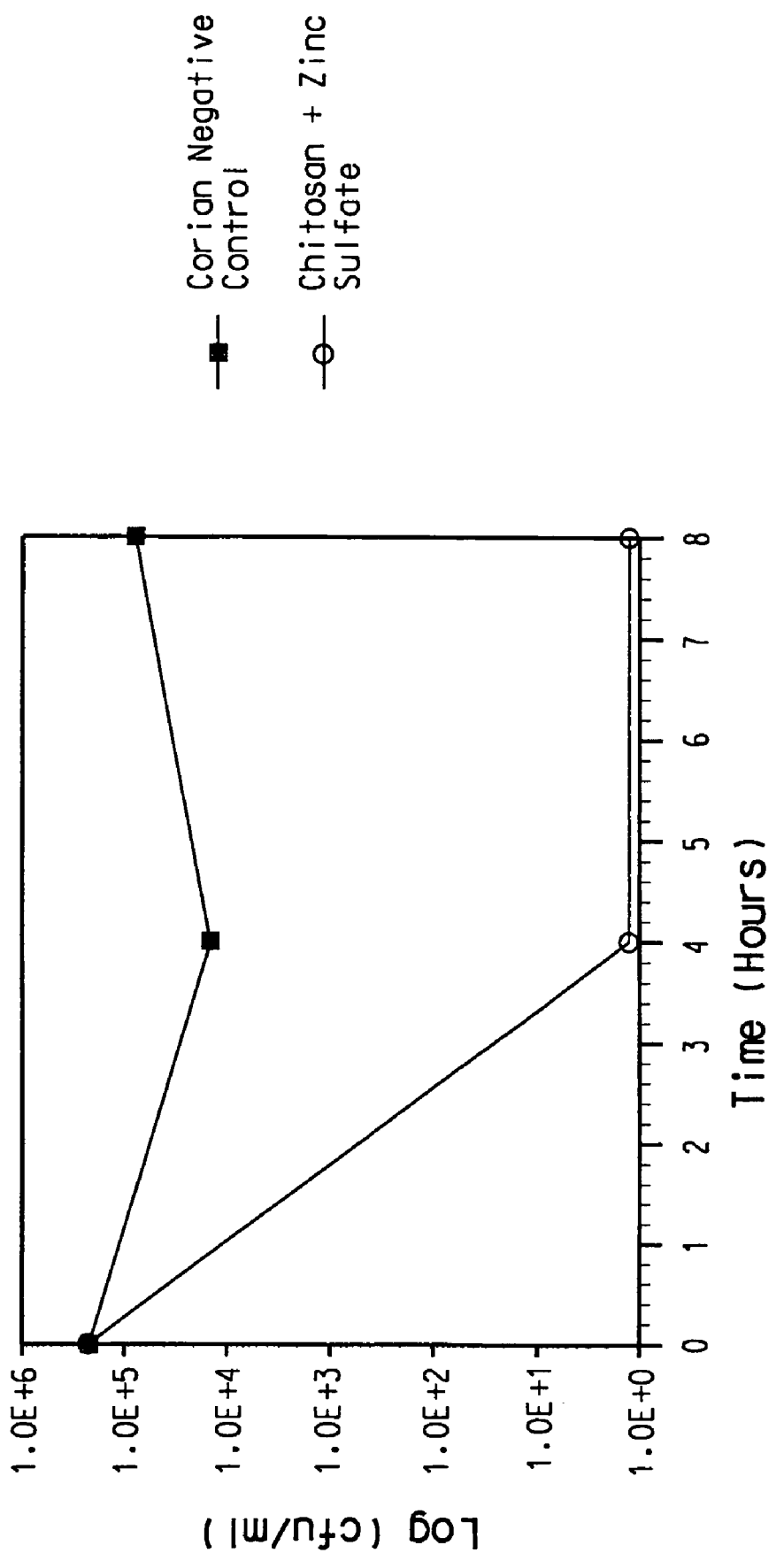
FIG. 14 shows the results of Corian® material with chitosan-zinc sulfate vs. *Candida albicans* (ATCC 10231).

Preparation of Chitosan-Zinc Sulfate for Use as Additives in Corian® Material Plaques Chitosan (40.5 g, ChitoClear®, Primex, Iceland) was dissolved in 2% aqueous acetic acid (1000 mL) and was vigorously stirred. To this, a solution of zinc sulfate (44.0 g) in water (100 mL) was added in drops. A viscous solution was obtained. To this, 250 mL of acetone was added to precipitate the product, which was filtered, washed with deionized water, and acetonitrile. It was dried under vacuum and ground to a fine powder (about 400 mesh size; 64 g). This preparation provided antimicrobial plaques against Gram positive and Gram negative bacteria as well as against yeasts as indicated in FIGS. 12, 13, and 14.

Example 7

Preparation of Chitosan-Copper Sulfate Complexes for Incorporation into Corian® Material Plaques Chitosan (20.0 g, ChitoClear®, Primex, Iceland) was dissolved in 1.5% aqueous acetic acid (650 mL) and was vigorously stirred. To this, a solution of copper sulfate (25.0 g) in water (140 mL) was added in drops. A fibrous precipitate was obtained, which was filtered, washed with deionized water, and acetonitrile. It was dried under vacuum and ground to a fine powder (42 g).

Figure 15:
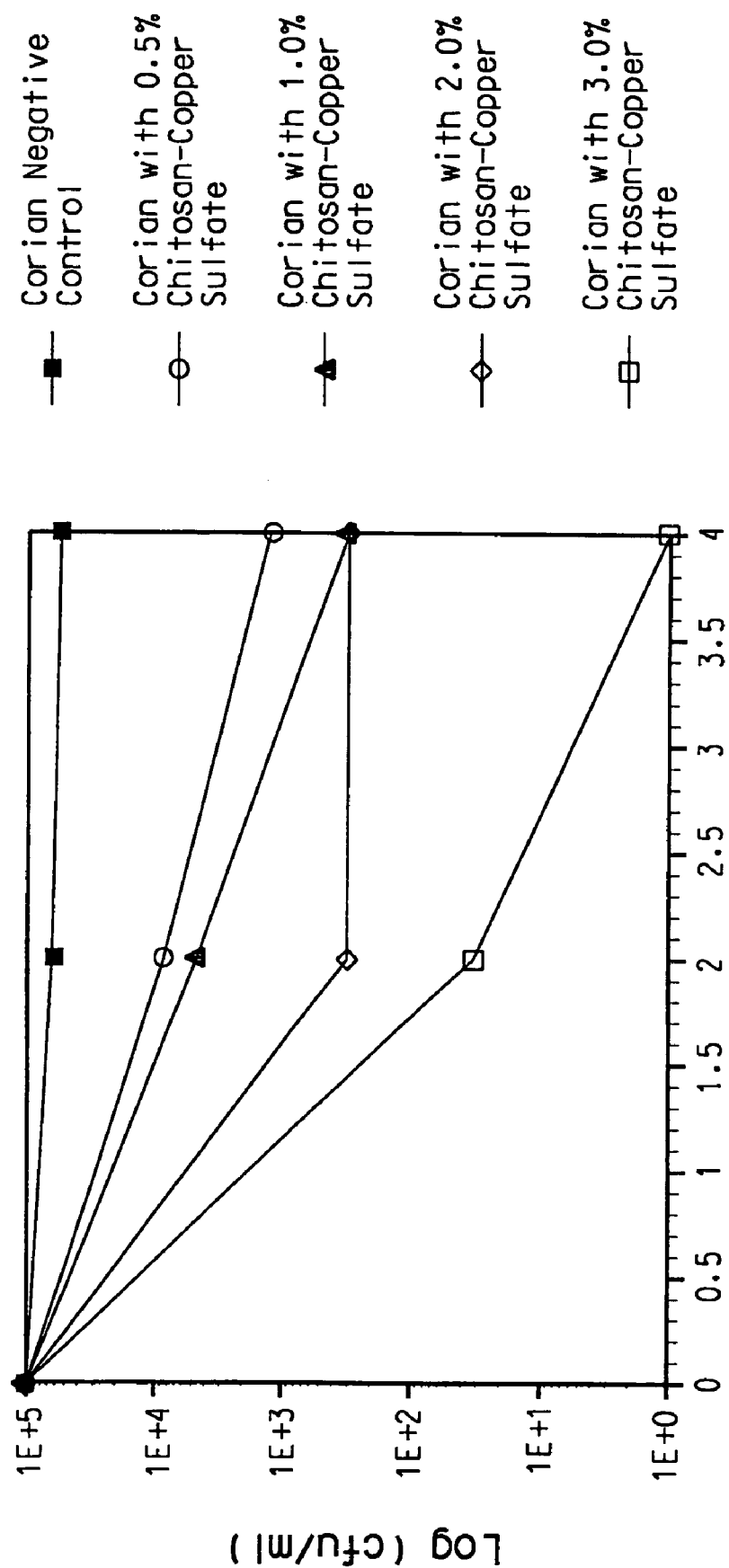
FIG. 15 shows the results of Corian® material with chitosan-copper sulfate vs. *Escherichia coli* (ATCC 25922).

Corian® material plaques containing 0.5%, 1.0%, 2.0%, and 3.0% concentration by weight of the chitosan-copper sulfate powder were prepared and evaluated for their antimicrobial properties (FIG. 15).

Example 8

Preparation of Chitosan-Silver Nitrate Complexes

Chitosan (150 g, ChitoClear®) food grade, Primex, Iceland) was dissolved in 1.3% aqueous acetic solution (3800 mL) and stirred vigorously. A solution of silver nitrate (14.5 g) in deionized water (75 mL) was added over a period of 10 min. A clear, thick gel resulted. Additional water (400 mL) was added to the gel and stirred for 30 min. Concentrated ammonium hydroxide was added in drops to raise pH to 7-8. The product was filtered, washed with water (2×1000 mL), and then stirred in acetonitrile (1000 mL), filtered, and washed again with acetonitrile (1000 ml). The resulting product was dried under vacuum for two days to get a fibrous product (195 g). This was ground to a fine powder under liquid nitrogen temperture. The amount of silver in the complex was determined by Inductively Coupled Plasma spectroscopy (ICP), which is an atomic emission spectroscopy method in which inductively coupled plasmas are used as the excitation source (see, for example, Inductively Coupled Plasma Emission Spectroscopy, pt. 1, P. W. J. M. Boumans, John Wiley & Sons (New York, N.Y.), 1987, pp. 2-3). ICP silver metal analysis of this material indicated the proportion of silver to be 4% by weight.

Example 9

Nonwoven Fabric Treated with Chitosan-Silver Complex Solution 0.9% Chitosan solution (ChitoClear® food grade, Primex, Iceland) in 0.5% aqueous acetic solution was made. Chitosan-silver powder (9.0 g) from Example 8 was added and dissolved to give a chitosan solution containing about 3600 ppm of silver. A nonwoven fabric (55% pine wood pulp/45% PET, 2 oz/yd$^2$) was passed through deionized water and then through the chitosan-silver solution, squeezed between rollers and dried in hot air (115° C.) and wound. This was tested for antimicrobial activity against *E. Coli* ATCC # 25922.

TABLE 2

| Sample | *E. coli* ATTC 25922 Log Reduction after 1 hour | *E. coli* ATCC 25922 Log Reduction after 4 hours | *E. coli* ATCC 25922 Log Reduction after 8 hours |
| --- | --- | --- | --- |
| Uninoculated buffer | 0 | 0 | 0 |
| Inoculated Buffer | −0.62 | −0.54 | −0.57 |
| Fabric with chitosan-silver complex | 5.1 | 5.1 | 5.1 |

What is claimed is:

1. A method for producing a chitosan-silver complex, the method comprising the sequential steps of: (a) dissolving 0.25 to 8.0% by weight chitosan in an acid solution; (b) adding a solution of a silver salt to the product of step (a); (c) adding water to the product of step (b), with stirring; (d) raising the pH of the product of step (c) to pH 7 to 8 by adding a basic solution; (e) filtering the product of step (d); (f) washing the filtered solids obtained in step (e) with water, (g) washing the solids of step (f) with acetonitrile; (h) drying the washed solids under vacuum to obtain the chitosan-silver complex; and (i) optionally, grinding the dried product of step (h) to a fine powder.

2. The method of claim 1, wherein the acid solution is a 0.25 to 5% aqueous solution of acetic acid; the silver salt solution is 0.5 to 20 wt % silver nitrate in water; and the pH is raised in step (d) by addition of aqueous ammonium hydroxide or substituted ammonium hydroxide.

3. A chitosan-silver complex produced by the method of claim 1.

4. A finish solution for textile applications comprising the chitosan-silver complex of claim 3.

* * * * *